United States Patent
Goodey et al.

(10) Patent No.: US 6,638,740 B1
(45) Date of Patent: *Oct. 28, 2003

(54) PROCESS OF HIGH PURITY ALBUMIN PRODUCTION

(75) Inventors: Andrew Robert Goodey, Mapperley Park (GB); Darrell Sleep, West Bridgford (GB); Hendrik Van Urk, Radcliffe-on-Trent (GB); Stephen Berezenko, Hucknall (GB); John Rodney Woodrow, West Bridgford (GB); Richard Alan Johnson, West Bridgford (GB); Patricia Carol Wood, Burton-on-Trent (GB); Stephen James Burton, Little Eversden (GB); Alan Victor Quirk, Loughborough (GB)

(73) Assignee: Delta Biotechnology Ltd., Castle Court (GB)

(*) Notice: Subject to any disclaimer, the term of this patent is extended or adjusted under 35 U.S.C. 154(b) by 0 days.

This patent is subject to a terminal disclaimer.

(21) Appl. No.: 08/952,558

(22) PCT Filed: Feb. 29, 1996

(86) PCT No.: PCT/GB96/00449

§ 371 (c)(1),
(2), (4) Date: Feb. 24, 1999

(87) PCT Pub. No.: WO96/37515

PCT Pub. Date: Nov. 28, 1996

Related U.S. Application Data

(63) Continuation-in-part of application No. 08/378,859, filed on May 25, 1995, now Pat. No. 5,728,553.

(51) Int. Cl.[7] ............................ C12N 15/14; C07K 14/00

(52) U.S. Cl. ............... 435/69.6; 530/362; 530/363; 530/364; 530/412; 530/413; 530/414; 530/416; 530/417; 530/420; 514/4; 514/12; 514/21

(58) Field of Search ............... 435/69.6; 530/362, 530/363, 364, 412, 413, 414, 416, 417, 420; 514/4, 12, 21

(56) References Cited

U.S. PATENT DOCUMENTS

| | | | |
|---|---|---|---|
| 2,433,905 A | 1/1948 | Hughes | 530/362 |
| 3,992,367 A | 11/1976 | Plan et al. | 530/362 |
| 4,007,113 A | 2/1977 | Ostreicher | 210/23 |
| 4,289,690 A | 9/1981 | Pestka et al. | 530/351 |
| 4,391,801 A | 7/1983 | Ng et al. | 424/177 |
| 5,346,992 A | 9/1994 | Grandgeorge et al. | 530/364 |
| 5,372,997 A | 12/1994 | Inoue et al. | 514/21 |
| 5,616,691 A | 4/1997 | Takahashi et al. | 530/364 |
| 5,728,553 A * | 3/1998 | Goodey et al. | 435/69.6 |
| 6,034,221 A * | 3/2000 | Berezenko et al. | 530/362 |

FOREIGN PATENT DOCUMENTS

| | | |
|---|---|---|
| CA | 2058676 | 8/1992 |
| DE | 2422426 | 5/1974 |
| EP | 0 249 483 B1 | 6/1987 |
| EP | 0 249 483 A2 | 6/1987 |
| EP | 361 991 | 4/1990 |
| EP | 420 007 A1 | 9/1990 |
| EP | 0 498 133 A1 | 1/1992 |
| EP | 0524681 * | 1/1993 |
| EP | 570916 * | 11/1993 |
| EP | 685 491 | 12/1995 |
| FR | 2 619 567 | 8/1988 |
| FR | 2672604 | 8/1992 |
| JP | WO 92/09303 | 6/1992 |
| JP | 4187700 A | 7/1992 |
| JP | 4210646 | 9/1993 |
| JP | 2982296 B2 | 11/1999 |
| WO | WO 92/04367 * | 3/1992 |
| WO | WO 93/17045 * | 9/1993 |

OTHER PUBLICATIONS

Quirk et al., *Biotech. and Applied Biochemistry*, vol. 11, pp. 273–287; 1989.*
Dodsworth, et al (1996) Biotechnol. Appl. Biochem 24, 171–176.
Co–Sarno et al (1983) *J Chromatog.* 266, 105–113.
Hansen & Ezban (1981) *Develop. Biol. Stand.* 48, 105–112.
Van Liederkerke et al (1991) *J. Pharm. Sci.* 80, 11–16.
Nesbakken (1982) "Comparative Study of Different Preparations of Human Albumin for Clinical Use", in "Compte–rendu de la réunion coopération internationale et dérivés sanguins", 1981, Annecy, France; Fondation Mérieux, Lyons.
Tayot et al (1982) "Comparative Study of Differnet Preparations of Human Albumin for Clinical Use", in "Compte–rendu de la réunion coopération internationale et dérivés sanguins", 1981, Annecy, France; Fondation Mérieux, Lyons.
Atkinson & Mavituna (1991) *Biochem Eng Biotechnol Handbook* (2nd Ed) Stockton Press: 935–937.
Bertholf et al (1984) *Bioch & Biophys Res Comm* 125(3): 1020–1024.
Cohn et al (1946) *J Am Chem Soc* 68: 459.
Dawson et al (1993) *Data for Biochem Res* (3rd Ed), Oxford University Press, Oxford, UK: 503–504.
Lee et al (1989) *Applied Biochem & Biotechnol* 22(1): 1–11.
Milliner et al (1985) *New Eng J Med* 312(21): 1389–1390.
Milliner et al (1985) *New Eng J Med* 312(3): 165–167.
Olsen & Kent (1989) *Transfusion* 29(1): 86–87.
Perry et al (1984) *Perry's Chemical Engineering Handbook* (6th Ed), McGraw–Hill Inc., New York, USA: 19.72–19.73.

(List continued on next page.)

Primary Examiner—Christopher S. F. Low
Assistant Examiner—Abdel A. Mohamed
(74) Attorney, Agent, or Firm—Arthur G. Seifert

(57) ABSTRACT

The present invention relates to a process for purifying the protein human serum albumin extracted from serum or recombinant human albumin produced by transforming a microorganism with a nucleotide coding sequence encoding the amino acid sequence of human serum albumin. The present invention provides highly purified albumin.

67 Claims, 7 Drawing Sheets

OTHER PUBLICATIONS

Petrie et al (1984) *Am J Kid Dis IV*, 1: 69–74.
Quagliaro et al (1988) *J Parenteral Sci & Tech* 42(6): 187–190.
Sattar et al (1979) *Water Res* 13(7): 637–643.
Victor et al (1988) *Transfusion* 28(3): 290–291.
Peters et al (1973) *J. Biol. Chem.* 248, 2447–2451.
Aslam et al (1976) *Anal. Biochem.* 751(1), 329–335.
Sundberg & Porath (1974) *J. Chromatog.* 90, 87–98.
"Affinity Chromatography", Pharmacia booklet, 1979, pp. 9, 12 and 27.

*Organikum*, VEB Deutcher Verlag der Wissenschaften, 5 Auflage, 1965, pp. 250.

Unger (1989) *Handbuch der HPLC*, GIT Verlag, pp. 74–75.

Kawabe (1991) "Study on the Development of a Human Serum Albumin Production System with Recombinant DNA Technology" (1990) *Japan Health Sciences Foundation, Tokyo, Japan,* Study Reports on Anti–AIDS Drug Development.

\* cited by examiner

1. OCTANOIC ACID (C8:0)
2. DECANOIC ACID (C10:0)
3. DODECANOIC ACID (C12:0)
4. TETRADECANOIC ACID (C14:0)
5. HEXADECANOIC ACID (C16:0)
6. cis-9-HEXADECANOIC ACID (C16:1)
7. HEPTADECANOIC ACID INTERNAL STD
8. OCTADECANOIC ACID (C18:0)
9. cis-9-OCTADECANOIC ACID (C18:1)
10. cis-9,12-OCTADECANOIC ACID (C18:2)
11. cis-9,12,15-OCTADECANOIC ACID (C18:3)
12. cis-5,8,11,14-EICOSATETRAENOIC ACID (C20:4)

1. OCTANOIC ACID (C8:0)
2. DECANOIC ACID (C10:0)
3. DODECANOIC ACID (C12:0)
4. TETRADECANOIC ACID (C14:0)
5. HEXADECANOIC ACID (C16:0)
6. cis-9-HEXADECANOIC ACID (C16:1)
7. HEPTADECANOIC ACID INTERNAL STD
8. OCTADECANOIC ACID (C18:0)
9. cis-9-OCTADECANOIC ACID (C18:1)
10. cis-9,12-OCTADECANOIC ACID (C18:2)

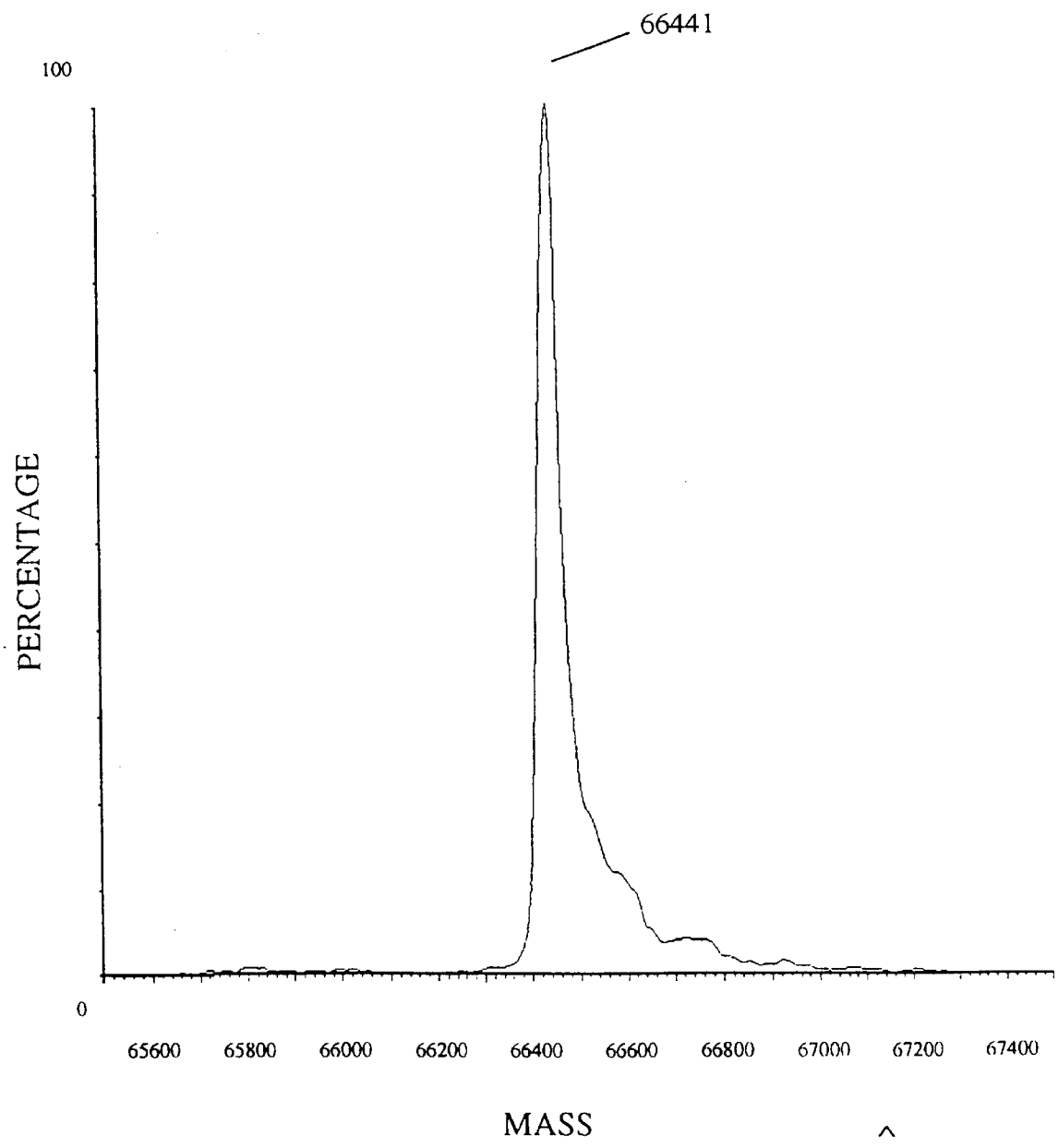
Figure 6a ESMS of rHA

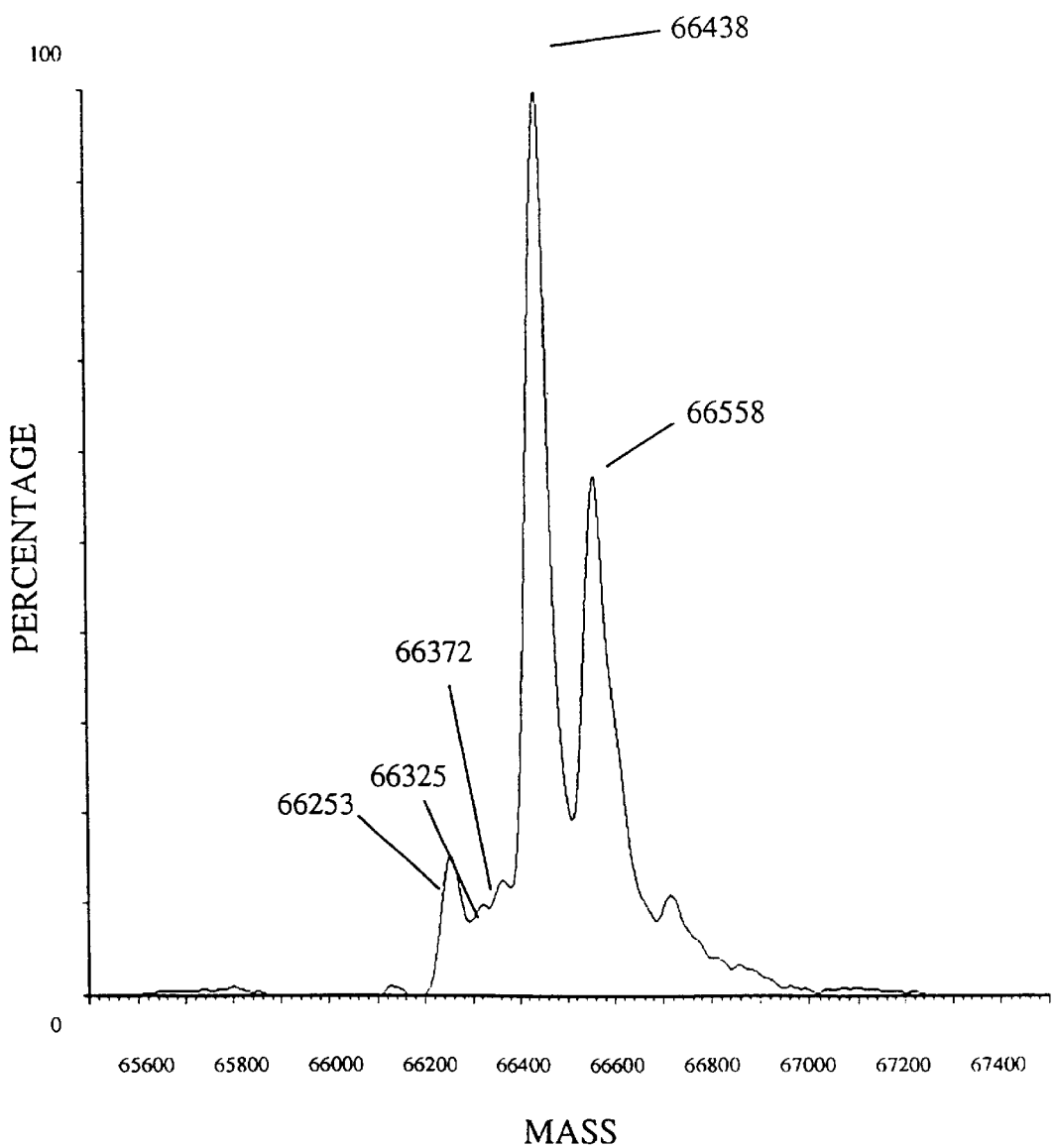
Figure 6b. ESMS of HSA.

SEQUENCE LISTING

<160> NUMBER OF SEQ ID NOS: 4

<210> SEQ ID NO 1
<211> LENGTH: 11
<212> TYPE: PRT
<213> ORGANISM: Homo sapiens

<400> SEQUENCE: 1

Leu Val Ala Ala Ser Gln Ala Ala Leu Gly Leu
1               5                   10

<210> SEQ ID NO 2
<211> LENGTH: 10
<212> TYPE: PRT
<213> ORGANISM: Homo sapiens

<400> SEQUENCE: 2

Leu Val Ala Ala Ser Gln Ala Ala Leu Gly
1               5                   10

<210> SEQ ID NO 3
<211> LENGTH: 6
<212> TYPE: PRT
<213> ORGANISM: Homo sapiens

<400> SEQUENCE: 3

Ala Trp Ala Val Ala Arg
1               5

<210> SEQ ID NO 4
<211> LENGTH: 8

-continued

```
<212> TYPE: PRT
<213> ORGANISM: Homo sapiens

<400> SEQUENCE: 4

Asp Leu Gly Glu Glu Asn Phe Lys
 1               5
```

PROCESS OF HIGH PURITY ALBUMIN PRODUCTION

This application is a continuation-in-part of U.S. application Ser. No. 08/378,859, filed May 25, 1995, now U.S. Pat. No. 5,729,553 the contents of which are hereby incorporated herein by reference.

The present invention relates to purifying the protein human serum albumin (HSA) extracted from serum or recombinant human albumin (rHA) produced by transforming a microorganism with a nucleotide coding sequence encoding the amino acid sequence of human serum albumin. In this specification, the term "albumin" refers generically to HSA and/or rHA.

DETAILED DESCRIPTION OF THE INVENTION

Albumin is used to treat patients with severe burns, shock or blood loss. It is also used to supplement media used for growing higher eukaryotic cells and as an excipient in the formulation of therapeutic proteins. At present, the demand for the product is satisfied by albumin extracted from human blood. Examples of extraction and separation techniques include those disclosed in: JP 03/258 728 on the use of a cation exchanger; EP 428 758 on the use of anion exchange followed by cation exchange; and EP 452 753 on the use of heating, adding salt and diafiltering.

BACKGROUND OF THE INVENTION

The production of rHA in microorganisms has been disclosed in EP 330 451 and EP 361 991. Purification techniques for rHA have been disclosed in: WO 92/04367, removal of matrix-derived dye; EP 464 590, removal of yeast-derived colorants: and EP 319 067, alkaline precipitation and subsequent application of the rHA to a lipophilic phase having specific affinity for albumin.

BRIEF SUMMARY OF THE INVENTION

The present invention relates to a process for purifying the protein human serum albumin extracted from serum or recombinant human albumin produced by transforming a microorganism with a nucleotide coding sequence encoding the amino acid sequence of human serum albumin. The present invention provides highly purified albumin.

The present invention provides highly purified albumin.

One aspect of the present invention provides a process for purifying albumin, the process comprising the steps of applying a relatively impure albumin solution to a chromatographic material for which the albumin has no specific affinity such that albumin binds to the material, and eluting the bound albumin from the material by applying a solution of a compound having a specific affinity for albumin. Preferably, the chromatographic material is a cation exchanger, such as SP-Sepharose FF, SP-Spherosil etc, as listed below in Example 2. The compound with specific affinity for albumin may be octanoate (eg sodium octanoate), other long chain ($C_6$ to $C_{22}$) fatty acids, salicylate, octylsuccinate, N-acetyltryptophan or a mixture of two or more of these.

A second aspect of the invention provides a process for purifying albumin, the process comprising the steps of subjecting an albumin solution to cation exchange chromatography in which the albumin is bound to a cation exchange material and then anion exchange chromatography in which the albumin is bound to an anion exchange material.

The albumin which is eluted from the cation exchange material may be subsequently treated by one or more of affinity chromatography, ultrafiltration and gel permeation before being subjected to the said anion exchange chromatography. Hence, in a preferred embodiment, the process comprises the steps of:

(a) passing an albumin solution through a cation exchange matrix under conditions such that the albumin will bind to the matrix:

(b) eluting from said matrix an albumin-containing cation exchange eluate:

(c) passing said eluate through an affinity matrix comprising an albumin-binding compound:

(d) eluting from said matrix an albumin-containing affinity matrix eluate:

(e) passing said eluate, optionally after ultrafiltration, through a gel permeation matrix to obtain a fraction enriched in albumin;

(f) passing the said albumin-enriched fraction through an anion exchange matrix under conditions such that albumin will bind to the matrix: and (g) eluting from said anion exchange matrix a purified albumin-containing product.

Alternatively, the albumin which is eluted from the cation exchange material may be applied to the said anion exchange material without any intervening treatment (other than dilution). Hence, a second preferred embodiment provides a process for purifying albumin, comprising the steps of:

(a) passing an albumin solution through a cation exchange matrix under conditions such that the albumin will bind to the matrix;

(b) eluting from the matrix an albumin-containing cation exchange eluate;

(c) passing the cation exchange eluate through an anion exchange matrix under conditions such that the albumin will bind to the matrix;

(d) eluting from the anion exchange matrix an albumin-containing anion exchange eluate;

(e) passing the anion exchange eluate through an affinity matrix comprising an albumin-binding compound;

(f) eluting from the affinity matrix an albumin-containing affinity matrix eluate;

(g) passing the affinity matrix eluate through a gel permeation matrix to obtain a fraction enriched in albumin.

Preferably, prior to the cation exchange step, the albumin solution is conditioned by adding octanoate and/or other albumin stabiliser (eg sodium acetyltryptophanate) thereto to a final concentration of from about 1–10 mM and adjusting the pH to about 4.0–5.0.

Advantageously, the albumin retained in the cation exchange step is washed with a high salt solution (eg 0.5–2.0 M NaCl buffered at pH 4.0 with 10–100 mM, preferably 20–40 mM for example 27 mM sodium acetate) before being eluted.

Preferably, in processes in which the cation exchange eluate is passed directly to the anion exchanger, the albumin is eluted in the cation exchange step using a buffer containing a compound having a specific affinity for albumin, especially an acid or salt thereof, for example octanoate or any other long chain ($C_6$–$C_{22}$) fatty acid. salicylate, octylsuccinate or N-acetyltryptophan.

Suitably, the albumin is eluted from the anion exchanger with a buffer containing a high level (eg at least 50 mM, preferably 50–200 mM, for example 80–150 mM) of a boric acid salt, for example sodium or potassium tetraborate.

The albumin purified in accordance with the invention may then, with or without intervening process steps, be subjected to chromatography on a resin containing an immobilised compound which will selectively bind glycoconjugates and saccharides, such as aminophenylboronic acid (PBA).

In any process of the invention which involves affinity chromatography, the affinity chromatography preferably uses a resin comprising an immobilised albumin-specific dye, such as a Cibacron Blue type of dye, preferably immobilised on the resin via a spacer such as 1,4-diaminobutane or another spacer of $C_{1-8}$, preferably $C_{1-6}$, eg $C_{1-5}$ and most preferably $C_4$ length, preferably having $\alpha,\omega$-diamino substitution. Surprisingly, we have found that such dyes actually have a greater affinity for a 45 kD albumin fragment which can be produced in cultures of HA-secreting microorganisms, than they do for the full length albumin molecule. The 45 kD fragment typically consists of the 1–403 to 1–409 region and is disclosed in Sleep et al (1990) Bio/Technology 8, 42–46 and in WO 95/23857.

The purified albumin solution prepared by the process of the invention may be further processed according to its intended utility. For example, it may be ultrafiltered through an ultrafiltration membrane to obtain an ultrafiltration retentate having an albumin concentration of at least about 80 g albumin per litre, with the ultrafiltration retentate being diafiltered against at least 5 retentate equivalents of water. It can be advantageous to include ammonium ions in certain chromatographic steps, for example in the step involving immobilised aminophenylboronate. Surprisingly, we have found that such ammonium ions are relatively tightly bound to the albumin. It is preferable for such ammonium ions to be removed from the albumin and we have found that this can be achieved by use of a counter-ion. The desirability of exposing the albumin to a counter-ion would not have occurred to those in this art since prior processes have not involved ammonium ions and there was no reason to suppose that ammonium ions would be bound by the albumin. Accordingly, a further aspect of the invention provides a method of purifying an albumin solution comprising exposing the solution to a solution of a counter-ion such that ammonium ions are displaced from the albumin and can be removed from the solution.

The counter-ion (preferably a metal ion such as sodium ions) can be added to the albumin solution and the ammonium ions removed by dialysis, or the ammonium ion can be diafiltered away across a semi-permeable membrane separating the albumin from the solution of the counter-ion, or they can be removed by gel permeation chromatography. Diafiltration against at least five retentate volumes of 50 mM sodium chloride is generally suitable.

The albumin obtained has been found to have extremely low levels of, or to be essentially free of, colorants, lactate,; citrate, metals, human proteins such as immunoglobulins, pre-kallikrein activator, transferrin, $\alpha_1$-acid glycoprotein haemoglobin and blood clotting factors, prokaryotic proteins, fragments of albumin albumin aggregates or polymers, endotoxin, bilirubin, haem, yeast proteins and viruses. By "essentially free" is meant below detectable levels. The term "colorant" as used herein means any compound which colours albumin. For example, a pigment is a colorant which arises from the organism, especially yeast, which is used to prepare recombinant albumin, whereas a dye is a colorant which arises from chromatographic steps to purify the albumin. At least 99%, preferably at least 99.9%, by weight of the protein in the albumin preparations purified by the process of the invention is albumin. Such highly pure albumin is less likely to cause adverse side effects.

The albumin produced by the process of the invention has been found to be at least 99.5% monomeric, preferably substantially 100% monomeric by reducing SDS PAGE, and is characterised by one or more of the following characteristics. It has an aluminium ion content of less than 150 ng, preferably less than 100 ng; an iron ion content of less than 3,000 ng, preferably less than 1,000 ng; a copper ion level of less than 10,000 ng, preferably less than 5,000 ng; a magnesium ion level of less than 3,000 ng, preferably less than 1,500 ng; a zinc ion level of less than 5,000 ng, preferably less than 3,000 ng, a manganese ion level of less than 50 ng, all based on one gram of albumin; a glycation level of less than 0.6, preferably less than 0.15 (more preferably less than 0.05), moles hexose/mole protein; a level of low molecular weight contaminants of below 20 V.sec, preferably less than 10 V.sec, measured as in Example 9 below; a single peak on a capillary zone electrophoretogram: intact, ie homogeneous, C-terminus and N-terminus: a free thiol content of at least 0.85 mole SH/mole protein; and no more than 0.3 mol/mol of C10 to C20 fatty acids and substantially no C18 or C20 fatty acids.

The starting material may be an albumin-containing fermentation medium, or the impure albumin solution may be a solution obtained from serum by any of the plethora of extraction and purification techniques developed over the last 50 years. for example those disclosed in Stoltz et al (1991) *Pharmaceut. Tech. Int.* Jun. 1991. 60–65 and More & Harvey (1991) in "*Blood Separation and Plasma Fractionation*" Ed. Harris, Wiley-Liss, 261–306.

Especially when the albumin is rHA produced in protease-deficient yeasts or other organisms, the process does not normally comprise a heat treatment step as part of the purification process (in contrast to EP 428 758 and EP 658 569). Similarly, if it is prepared from microorganisms (rather than from humans) it does riot normally require a final pasteurisation step (typically 60° C. for one hour).

The final product may be formulated to give it added stability. Preferably, the highly pure albumin product of the invention contains at least 100 g, more preferably 1 kg or 10 kg of albumin, which may be split between a plurality of vials.

Although the process of the present invention can be utilised to obtain more purified albumin from an impure albumin solution from a number of sources, such as serum, it is particularly applicable to purifying recombinant human albumin (rHA). The albumin produced in accordance with the invention may be any mammalian albumin, such as rat, bovine or ovine albumin, but is preferably human albumin. DNA encoding albumin may be expressed in a suitable host to produce albumin. Thus, DNA may be used in accordance with known techniques to construct an expression vector, which is then used to transform an appropriate host cell for the expression and production of albumin. Such techniques include those disclosed in EP-A-73 646. EP-A-88 632. EP-A-201 239 and EP-A-387 319.

Many expression systems are known, including bacteria (for example *E. coli* and *Bacillus subtilis*), yeasts (for example *Saccharomyces cerevisiae. Pichia pastoris* and *Kluyveromyces lactis*), filamentous fungi (for example Aspergillus), plant cells. animal cells and insect cells. The preferred microorganism is the yeast *Saccharomyces cerevisiae*.

Exemplary genera of yeast contemplated to be useful in the practice of the present invention are Pichia (Hansenula), Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis, and the like. Preferred genera are those selected from the group consisting of Pichia (Hanseniula), Saccharomyces, Kluyveromyces, Yarrowia and Hansenula. Examples of Saccharomyces spp. are *S. cerevisiae. S. italicus* and *S. rouxii*. Examples of Kluyveromyces spp. are *K. fragilis* and *K. lactis*. Examples of Pichia (Hansenula) are *P. angusta* (formerly *H. polymorpha*), *P. anomala. P. pastoris* and *P. capsulata. Y. lipolytica* is an example of a suitable Yarrowia species.

It is advantageous to use a yeast strain which is deficient in one or more proteases. Such strains include the well-known pep4-3 mutants and strains with mutations in the PRA1 and/or PRB1 genes, as in Woolford et al (1993) *J. Biol. Chem.* 268, 8990–8998, Cabezon et al (1984) P.N.A.S. 81, 6594–6598, EP-A-327 797 and Jones et al (1982) Genetics 102, 665–677. Alternatively, the proteases in the fermentation medium may be inactivated by heating. The existence of proteases reduces the yield of the albumin during the overall process. Preferably, the yeast has a low (or zero) level of the Yap3p protease and/or of the hsp150 heat shock protein, for example as a result of having the respective genes disrupted, as is taught in our patent applications published as WO 95/23857 and WO 95/33833. respectively. Yap3p can cause the formation of the 45 kD albumin fragment referred to below, and hsp150 co-purifies with albumin in some separation steps.

Yeast may be transformed with an expression plasmid based on the Saccharomyces cerevisiae 2μm plasmid. At the time of transforming the yeast, the plasmid contains bacterial replication and selection sequences, which may be excised, following transformation, by an internal recombination event in accordance with the teaching of EP 286 424. The plasmid may also contain an expression cassette comprising: a yeast promoter (such as the *Saccharomyces cerevisiae* PRB1 promoter), as taught in EP 431 880: a sequence encoding a secretion leader, for example one which comprises most of the natural HSA secretion leader, plus a small portion of the S. cerevisiae α-mating factor secretion leader as taught in WO 90101063: the HSA coding sequence obtainable by known methods for isolating cDNA corresponding to human genes, and also disclosed in, for example, EP 73 646 and EP 286 424; and a transcription terminator, for example the terminator from Saccharomyces ADH1, as taught in EP 60 057.

The choice of various elements of the plasmid described above is not thought to be directly relevant to the purity of the albumin product obtained although the elements may contribute to an improved yield of product.

Preferred aspects of the invention will now be described by way of example and with reference to the accompanying drawings, in which:

BRIEF DESCRIPTION OF THE DRAWINGS

FIGS. 6a and 6b show electrospray mass spectrometry for albumin of the invention and prior art albumin, respectively.

EXAMPLE 1

Preparation of Impure Albumin Solution

Figure 1:
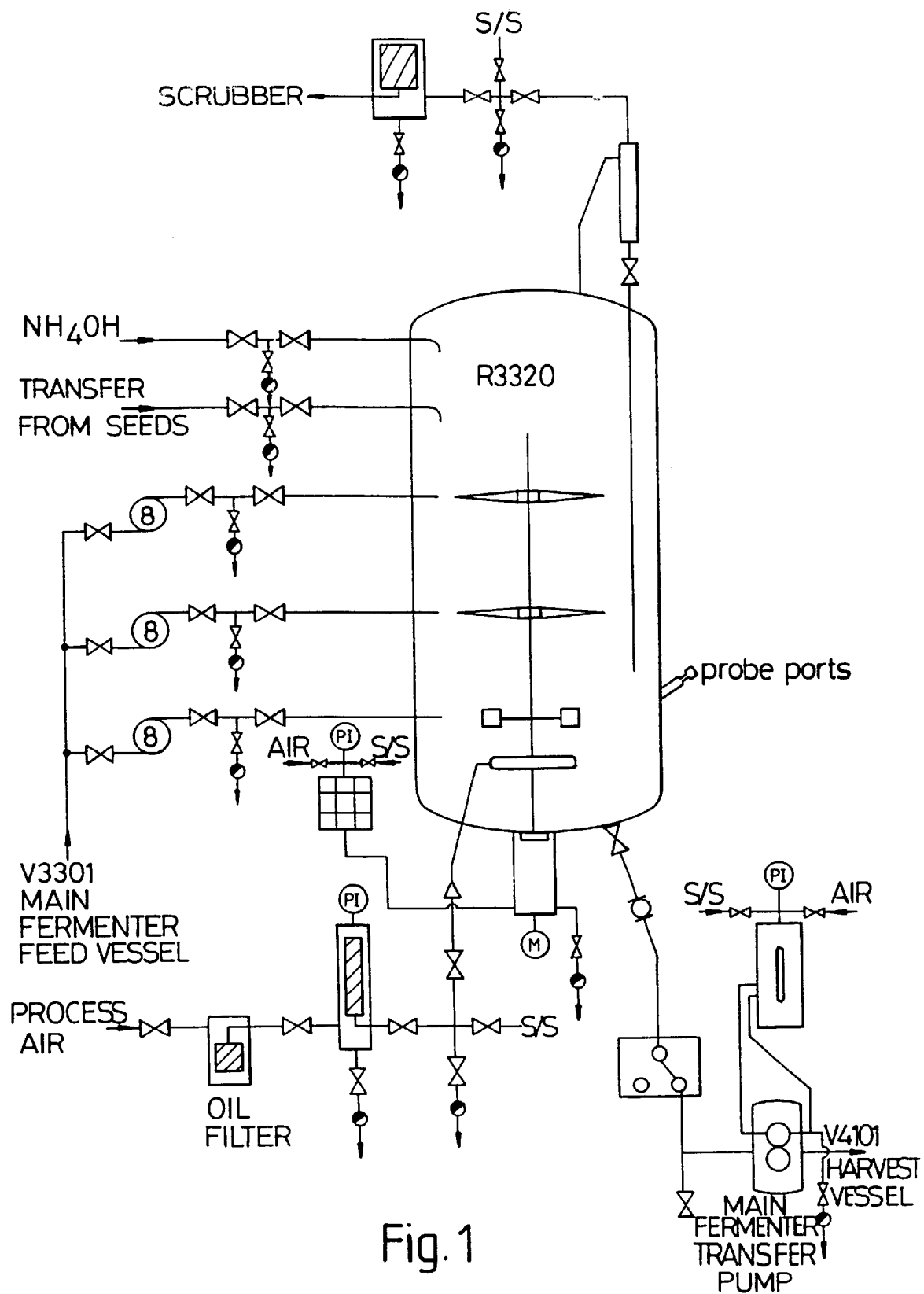
FIG. 1 shows schematically a fermenter used to produce rHA.

The cloning strategy for construction of the albumin-producing microorganism was as disclosed in EP 431 880. Plasmid pAYE316 was introduced into a (MATa, leu2, pep4-3, [cir*]) *Saccharomyces cerevisiae* strain by the method described by Hinnen et al, (1978) P.N.A.S. 75, 1929. Transformants were selected on a minimal medium lacking leucine (Yeast nitrogen base, Difco). When transformants were grown for 72 hours at 30° C., 200 rpm in 50ml flasks containing either 10 ml of complex (YEP, 1% (w/v) yeast extract, 2% (w/v) bactopeptone and 2% (w/v) sucrose), or defined (0.15% (w/v) yeast nitrogen base without amino acids and ammonium sulphate, 0.5% (w/v) ammonium sulphate, 0.1M citric acid/$Na_2HPO_4$, $12H_2O$ pH6.5, 2% (w/v) sucrose) liquid medium, rHA could be detected in the cell free culture supernatant by SDS-polyacrylamide gel electrophoresis and/or by rocket gel immunoelectrophoresis.

A stock master cell culture in defined liquid medium (Buffered Minimal Medium (BMM) salts medium: Yeast Nitrogen Base [without amino acids and $(NH_4)_2SO_4$, Difco], 1.7 g/L; citric acid monohydrate 6.09 g/L; anhydrous $Na_2HPO_4$, 20.16 g/L, pH 6.5±0.2, sucrose is added to 20 g/L) is used to prepare running stocks (manufacturer's working cell bank) of process yeast suitable for the preparation of shake flask cultures by freezing aliquots of the culture in the presence of 20% (w/v) trehalose.

Fermentation

This section relates to the production of rHA from stock culture through to the final fermentation and is a general definition of an rHA fermentation process which is not limited to the specific detail of particular equipment or scale.

Shake Flask Culture. The yeast [cir°, pAYE316] is grown as an axenic culture physiologically suited for inoculation of the seed vessel. If timing of the seed vessel is to be reproducible, it is necessary to define the phase of growth (primary carbohydrate excess) and inoculum biomass (12±2mg/L which requires a 100 ml inoculum per 10 litres of medium). One stock vial is inoculated into a shake flask containing 100 mL of BMM+2%(w/v) sucrose and the flask is incubated at 30° C. on an orbital shaker (200 rpm revolutions per minute) until a cell dry weight (cdw) of 0.6–1.2 g/L (assessed by optical density at 600 nm) is obtained. This culture is then used to inoculate a seed fermentation vessel to a level of 12±2 mg/L.

Seed Fermentation. The inoculum for the main production fermenter is provided by growing the production organism, preferably *S. cerevisiae* [cir°, pAYE316], in a seed fermenter (in this example, 20 L working volume) to a high cell dry weight (cdw) of approx. 100 $gL^{-1}$. A fed-batch regime is followed so as to minimise the accumulation of ethanol and acetate and thus to maximise cell yield. The whole of each fermentation is monitored and controlled via a computer control system, such as the Multi-Fermenter Computer System (MFCS) software available from B. Braun (Germany). The software supplied by B. Braun is a Supervisory Control and Data Acquisition Package; similar packages are available from other companies. The feed control algorithm is intended to control the addition of sucrose so that maximum biomass is achieved by avoiding the Crabtree effect, thereby minimising the production of ethanol and/or acetate. The fermentation vessel is subjected to a hot NaOH wash and pyrogen-free water (PFW) rinse. The heat sterilised vessel will contain approximately 10 L of sterile MW10 medium (Table 1) batch salts plus trace elements. The medium for rHA production can be ultrafiltered (10.000 Mol. Wt. cut-off) to remove endotoxins.

TABLE 1

MW10 MEDIUM

| Constituents | Batch Medium | Feed Medium |
|---|---|---|
| Salts | | |
| $KH_2PO_4$ | 2.74 g/L | 10.9 g/L |
| $MgSO_4.7H_2O$ | 0.58 g/L | 2.3 g/L |
| $CaCl_2.2H_2O$ | 0.06 g/L | 0.24 g/L |
| $H_3PO_4$(85% w/w) | 0.88 ml/L | 1.76 ml/L |
| Vitamins | | |
| Ca pantothenate | 20 mg/L | 180 mg/L |
| Nicotinic acid | 33.3 mg/L | 300 mg/L |
| m-Inositol | 20 mg/L | 180 mg/L |
| d-biotin | 0.133 mg/L | 0.8 mg/L |
| Thiamine.HCl | 16 mg/L | 32 mg/L |
| Trace element stock | 10 ml/L | 20 ml/L |
| Sucrose | 0* | 500 g/L |
| Trace Element Stock Constituents | | |
| $ZnSO_4.7H_2O$ | | 3 g/L |
| $FeSO_4.7H_2O$ | | 10 g/L |
| $MnSO_4.4H_2O$ | | 3.2 g/L |
| $CuSO_4.5H_2O$ | | 0.079 g/L |
| $H_3BO_3$ | | 1.5 g/L |
| KI | | 0.2 g/L |
| $Na_2MoO_4.2H_2O$ | | 0.5 g/L |
| $CoCl_2.6H_2O$ | | 0.56 g/L |

The trace elements are added to demineralised water, acidified with 35 ml/L of 98% $H_2SO_4$.
*20 g Sucrose/L is added to the batch medium at the 20 L seed fermenter stage. Any convenient method of sterilisation may be used, as may any depyrogenation method, for example ultrafiltration. The vitamins are always filter sterilised.

After the medium is added to the vessel, the operating temperature of 30° C. is set, as well as the minimum stirrer speed, typically 400–500 rpm. The initial pH is adjusted with ammonia solution (specific gravity 0.901) using a pH controller set at 5.7±0.2. 2M $H_2SO_4$ is also used as a pH corrective agent. Sucrose to 20 $gL^{-1}$, MW10 batch vitamins, and Breox FMT30 antifoam to 0.04$gL^{-1}$ are added to the vessel.

Sterile filtered air is introduced into the vessel at 0.5 v/v/m (ie 0.5 litre non-compressed air per litre of medium per minute), the medium is inoculated to 12±2mg cell dry weight $L^{-1}$ from an axenic shake flask culture and the MFCS computer system is initiated. Following completion of the batch phase of growth (signalled by a dissolved oxygen tension increase of >15% in 30 min), addition of the feed medium is initiated, under control of the MFCS system. The control strategy is effectively the same as described below for the production fermentation. During the fermentation the air flow is increased in two steps in order to maintain a flow of approximately 1 v/v/m. The dissolved oxygen tension (DOT) is controlled at 20% air saturation by changing the stirrer speed. Once the stirrer speed cannot be increased further and the air flow rate has reached its maximum value, the feed control algorithm controls the feed rate to minimise the formation of fermentation products. At the end of the feed, the culture is transferred to a production vessel.

Production Fermentation. An axenic culture of the yeast [cir*, pAYE316] is produced by fed-batch fermentation to a high cdw (>80 $gL^{-1}$) for the production of extracellular rHA. The production fermenter, in this example a fermenter with a working volume of 8,000 L, is inoculated with the culture grown in the seed fermenter, the cell dry weight of which is preferably >80 $g.L^{-1}$. The initial cell dry weight concentration in the production fermenter on transfer of the seed fermenter culture is preferably 0.25–1.00 $g.L^{-1}$. Although it is preferred to initiate feeding within one hour, it can be delayed if necessary. Due to the very low values of OUR and CER during the initial part of the feed phase and the consequent errors in their measurement, the automatic control of feed rate using RQ is initially disabled. The feed regime is intended to minimise the accumulation of ethanol and acetate, so as to maximise the cell and product yield.

The fermentation is carried out in a fermenter such as that shown in FIG. 1, designed to give optimum gas dissolution and bulk mixing. The vessel, which is subjected to a hot NaOH wash and PFW rinse, will contain approximately 4000 L of sterile MW10 (Table 1). batch salts and trace elements. This medium may be sterilised independently of the vessel either by heat or filter sterilisation. It has been found in accordance with the present invention that it is advantageous for the fermentation medium, such as MW10, to be free of ethylene diamine tetraacetic acid (EDTA), or a salt thereof or other strong metal-chelating agents, since their presence results in a significantly higher degree of coloured contaminants in the albumin produced.

The operating temperature is set at 30° C. and the stirrer speed regulated to be sufficient to maintain a homogeneous solution, typically about 50 rpm. The initial pH is adjusted with ammonia solution (SG 0.901) (controller set to 5.7±0.2). 2M $H_2SO_4$ may be used as a second pH corrective agent. The MW10 batch vitamins are added, as is a suitable antifoam, as required (eg Breox FMT30 to 0.125 $gL^{-1}$).

Sterile filtered air is added to the vessel at 0.5 v/v/m initially to maximise sensitivity of exhaust gas analysis, and the MFCS computer system is initiated. The exhaust gas is analysed, for instance by use of a continuous mass spectrometer (eg a Fisons VG gas analyzer). The vessel is inoculated with the whole of the seed vessel culture (minimum 0.4% v/v). MW10 feed in a volume equal to the batch volume. The feed is started and the RQ override control disabled until OUR and CER values are sufficiently high to make control effective. The feed rate is adjusted manually during the period without RQ control if RQ is consistently >1.2. The feed rate is increased, via computer control, according to the following algorithm:

$$\text{Feed rate (FR)} = ke^{\mu t}$$

where k is the initial feed rate, $\mu$ is the exponential growth rate, and t is time. The value k is determined empirically as the initial feed rate that is necessary to achieve a growth rate that minimises the accumulation of ethanol and acetate. For this example, k has been determined as having a value 0.08 mL of MW10 feed medium per minute per liter of culture. The value $\mu$ is related to the maximum growth rate of a fully respirative organism, in this example 0.1 $h^{-1}$.

t is a counter variable that starts at 0 (zero) and then increases by 1 every minute, unless RQ>1.2 or DOT<15%. In these cases, the value of t is reduced.

The vessel can be overpressured as necessary to enhance OTR. The culture is held for downstream processing at the end of the feed.

This hold time should be kept to a minimum, but can be extended up to 48 hours and beyond if necessary. During the hold phase, the temperature of the culture is reduced to the minimum possible, typically between 4 and 15° C., preferably 4° C., and the DOT is allowed to fall to 0%. The feed is stopped, the aeration turned off and the overpressure reduced. The pH control, however, is maintained. Sufficient agitation is maintained to retain the cells in suspension and facilitate cooling and pH homogeneity, preferably about 50 rpm.

The expected yields in accordance with the above procedure are: biomass >80 g cell dry weight/L culture; rHA >1.5 g monomer/L culture (determined by SDS-PAGE, related to the whole culture).

In order to prepare an impure albumin solution for purification treatment in accordance with the present invention when the albumin is rHA, the microorganism cells are removed from the fermentation culture medium. While it is preferred that the cells be removed prior to beginning of the purification process as described, it can be carried out simultaneously with the first step under certain conditions, eg where the first purification step is carried out in a fluidised bed. The fermentation culture, which has been cooled in the fermenter during the hold phase to less than 15° C. without aeration, is transferred to a tank where it is diluted to give a biomass concentration of 180–210 g/kg and cooled further if necessary. The diluted culture should be held for as short a time as possible without aeration at reduced temperature with sufficient agitation to prevent yeast cell deposition.

Cells and supernatant are subjected to a primary separation step, for example microfiltration or centrifugation in any appropriate centrifuge such as an Alfa Laval BTUX510 continuous discharge nozzle run at 5700 rpm. Centrate so produced may be filtered in line, for example using a depth filter (1 $\mu$m pore size), supplied by Cuno, to remove residual whole and broken yeast cells and other particles. At least 75% of the rHA present in the diluted culture is recovered in a single pass centrifugation operation. Optionally, the cell slurry from this operation may be resuspended in water or buffer and re-centrifuged to provide a second centrate. thus enhancing product recovery. The resultant solution is then treated by the process of the invention to purify the albumin contained therein as shown in Example 2.

EXAMPLE 2

Purification of Albumin in Accordance with the Invention

The centrate from a fermentation (such as described in Example 1), or an impure albumin solution from any other source (such as plasma), is prepared, or conditioned, for chromatography on a cation exchange matrix while protecting the albumin from polymerisation (by including octanoate) and protease activity (by heating or by choosing yeast without damaging levels of proteases). Preferably, sodium octanoate is added (Chromatography Solution 13 (CS13) - Table 2) to a final concentration of 1–10 mM, for example approximately 5 mM, to stabilise the albumin. The pH is adjusted with acetic acid (CS09) to 4.3–4.8, preferably 4.50±0.1 (most preferably ±0.05), and the conductivity is checked to be <5.5 mS cm$^{-1}$.

The culture supernatant from some host strains or species contains proteases that can degrade rHA during subsequent processing. In such instances, this protease activity can be destroyed by heat treatment of the culture supernatant containing the rHA. Typically 1–10 mM sodium octanoate is sufficient to protect the rHA from heat denaturation and 30 seconds up to 10 minutes at temperatures of 60–80° C. is adequate to inactivate the proteases. Subsequently the supernatant can be further conditioned as described previously. If degradation by proteases is not encountered, then the heat treatment is preferably omitted.

Chromatography

All operations can be carried out at ambient temperature (20±5° C.). The albumin loads (g albumin/L matrix) for the chromatography columns are determined from titres of albumin (g/L) by either SDS-PAGE (in the case of the SP-FF column) or GP-HPLC (for all other columns). The progress of each step is monitored by measuring UV absorbance on line, for example at 254 or 280 nm.

The sequence of chromatographic steps as described here is novel and inventive in a number of aspects. The use of a cationic matrix for the first purification step allows the majority of low molecular weight pigmented species derived from the yeast fermentation to pass directly through the column, whereas those that do bind to the matrix are bound weakly and can be removed by a high ionic strength salt clean such as 1M NaCl. Thus the cationic matrix, unlike an anionic matrix which adsorbs these type of molecules irreversibly, can be regenerated and used for multiple cycles of chromatography as the first step in the purification. Hence, this step forms the basis for a robust commercial chromatography process.

The use of a Cibacron Blue type of column as the second step in this example is novel in that it is used specifically to remove a 45kDa fragment of albumin which is very difficult to remove from albumin as its physicochemical properties, eg size and pI, are similar to the intact molecule. Surprisingly, the fragment binds more strongly to the dye than full length albumin does, thus allowing their separation.

The chromatography solutions used during the purification of albumin are detailed in Table 2. Because of the very large scale manufacture of albumin, and the relatively low cost of the product, these buffer salts are the most suitable for the process as they are available in a highly pure form at industrial scale and are low cost compared to other commonly used buffers such as Tris, HEPES or MOPS. Alternative buffers could be used in place of the ones used in Table 2. for example buffers of a similar $pk_a$ (eg malate for acetate), but in most instances cost and availability at large scale rule out their use. Alternative salt forms can be used provided they are soluble, available at industrial scale and low cost. However, the inclusion of tetraborate ions in CS06 and CS10 is particularly advantageous since they perform a specific role in complexing with carbohydrate moieties in macromolecules and binding them tightly to the anionic groups on the matrix. This results in an enhanced purity of albumin in the eluate.

Chromatography can be performed using either axial flow columns, such as those available from Pharmacia, or using radial flow columns, such as those available from Sepragen. In this example, the columns are all axial.

The buffer solutions can be prepared at the concentrations described below, or concentrated stock solutions can be prepared and mixed or diluted on-line for immediate use.

TABLE 2

CHROMATOGRAPHY SOLUTIONS FOR THE PURIFICATION OF ALBUMIN IN EXAMPLE 2

| Solution | Constituent | Concentration (gL$^{-1}$) | pH | Conductivity (mS cm$^{-1}$) |
|---|---|---|---|---|
| CS01 SP-FF Equilibrant | $CH_3COONa.3H_2O$ | 3.69 | 5.45–5.65 | 1.9–2.2 |
|  | $CH_3COOH$ (glacial) | 0.220 |  |  |
| CS02 SP–FF Eluent | $CH_3COONa.3H_2O$ | 13.6 | 5.45–5.65 | 6.5–7.5 |
|  | $CH_3COOH$ (glacial) | 0.750 |  |  |
| CS03 DBA Eluent | NaCl | 117 | 9.0–9.4 | 125–165 |
|  | $CH_3COONH_4$ | 3.84 |  |  |
|  | NaOH | 0.680 |  |  |
| CS04 0.5 M NaOH | NaOH | 20.0 | >12 | 80–120 |
| CS05 Gel Permeation | $CH_3COONa.3H_2O$ | 4.94 | 5.4–5.6 | 2.9–3.3 |
|  | $CH_3COOH$ (glacial) | 0.380 |  |  |
|  | Octanoic Acid | 0.721 |  |  |
|  | NaOH | 0.190 |  |  |
| CS06 DE-FF Eluent | $Na_2B_4O_7.10H_2O$ | 7.62 | 8.9–9.3 | 11.7–13.5 |
|  | NaCl | 5.84 |  |  |
| CS07 20 mM NaOH | NaOH | 0.800 | >12 | 3.5–5.5 |
| CS08 DE-FF Equilibrant | $CH_3COONa.3H_2O$ | 4.94 | 5.4–5.6 | 2.9–3.3 |
|  | $CH_3COOH$ (glacial) | 0.380 |  |  |
|  | Octanoic Acid | 0.721 |  |  |
|  | NaOH | 0.190 |  |  |
| CS09 Acetic Acid | $CH_3COOH$ | Glacial | — | — |
| CS10 DE-FF Wash | $Na_2B_4O_7.10H_2O$ | 7.62 | 9.0–9.4 | 2.3–2.9 |
| CS11 DE-FF Pre-equilibrant | $CH_3COONa.3H_2O$ | 61.8 | 5.5–5.7 | 24–28 |
|  | $CH_3COOH$ (glacial) | 2.98 |  |  |
| CS12 DBA Equilibrant/Wash | NaCl | 11.7 | 8.8–9.2 | 18–22 |
|  | $CH_3COONH_4$ | 0.960 |  |  |
|  | NaOH | 0.150 |  |  |
| CS13 2 M Sodium Octanoate | Octanoic Acid | 288 | 7.7–8.2 | — |
|  | NaOH | 76.0 |  |  |
| CS14 1.73 M Phosphoric acid | $H_3PO_4$ (85 % (w/w)) | 200 | <1.2 | — |
| CS15 2 M Ammonia | $NH_4OH$ (30% $NH_3$ (w/w)) | 113 ml | — | — |

All weighings are ±2%, for this particular example.

Cation Exchange Chromatography. Albumin is concentrated and purified with respect to at least yeast proteins (if the albumin is rHA from a yeast fermentation) and other antigens, low molecular weight contaminants and pigmented compounds by cation exchange chromatography. The method uses a commercial cation exchange matrix such as SP-Sepharose FF, SP-Spherosil, CM-Sepharose FF, CM-Cellulose, SE-Cellulose or S-Spherodex. Preferably the matrix is SP-Sepharose FF (Pharmacia) at a bed height of 5 to 25cm, preferably 10 to 15 cm and in this example 12.5 cm, with a column loading of 10 to 50 g albumin/L, preferably 40±10 g albumin/L matrix. The matrix is equilibrated with a buffer to remove the alkali storage solution; preferably the buffer should be strong enough to reduce the pH to approximately pH6.0. A buffer such as CS01 is used to remove storage solution CS07 from the column; however, any buffer with a pH <6.0 could be used. Equilibration is judged to be complete when the pH of the column effluent is approximately pH6.0.

The conditioned centrate is then loaded onto the column at a flow rate of, for example 1.0–8.0 cm/min, preferably 4.0–7.0 cm/min, in this example, 6.36 cm/min, and then the column is washed with a solution to remove residual contaminants. This wash solution should have a pH <6.0 and a conductivity less than 5 mS cm$^{-1}$, preferably less than 3 mS cm$^{-1}$, to prevent the elution of albumin. A suitable solution is CS01. The preceding steps are all run at 6.36 cm/min; for elution and all subsequent steps the flow rate is reduced to 0.5–5.0 cm/min, preferably 2.0–4.0 cm/min, in this example 3.18 cm/min, in order to reduce the volume of eluate. Elution of albumin is effected by increasing the ionic strength; a solution with a conductivity in the range 5–10 mS cm$^{-1}$, preferably 6–8 mS cm$^{-1}$, for example CS02, is used. The collection of albumin starts when the UV signal rises above 1.0 A$_{280}$/cm, and collection continues until the UV signal falls below 0.6 A$_{280}$/cm or a maximal volume of 6.5 column volumes has been collected. The column is then cleaned using CS03 and 04, and then stored in CS07.

Affinity Chromatography. This step further purifies the albumin with respect to a 45 kDa N-terminal albumin fragment, yeast antigens (if the albumin is rHA from a yeast fermentation) and pigment. The affinity matrix may comprise any Cibacron Blue type of dye which binds albumin, for example Reactive Blue 2, Procion Blue HB, Blue Sepharose, Blue Trisacryl and other anthraquinone-type compounds. Preferably, the matrix is the "Delta Blue Agarose" matrix described below. This has been found to reduce the levels of Blue leachates generated by the matrix and to enhance the alkaline stability of the matrix to facilitate cleaning and depyrogenation. A further improvement of the matrix compared to commercially available matrices is the incorporation of a spacer. 1,4-diaminobutane, between the dye (Reactive Blue 2) and the matrix. This was found to be the optimal length of spacer with respect to eluate albumin purity.

Reactive Blue 2 has the chemical structure represented below.

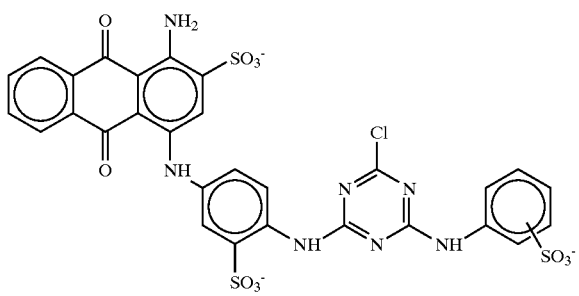

The ortho, meta or para isomer, or any mixture thereof, can be used. The preferred isomer is the ortho-$SO_3$ form but, as it is difficult to make to the desired purity, the meta isomer is used. The aminobutyl-Reactive Blue 2 is prepared to a minimum purity of 98% total peak area as determined by analytical HPLC. This can be achieved either by using crude commercially available dye, which will necessitate purification of the aminobutyl derivative dye, or using a pure synthesised dye. In the latter method, the starting dye material should be a minimum of 98% pure by analytical HPLC at 280 nm. Such material is available from ACL, Isle of Man. Reactive Blue 2 is reacted with 1,4-diaminobutane in water by heating the mixture to 60° C., after which the derivatised dye is purified from the mixture, for instance by precipitation. The aminobutyl-Reactive Blue 2 is then coupled to the matrix, for instance to epichlorhydrin-activated Sepharose CL-6B (Pharmacia, Sweden). See Porath et al (1971) *J. Chromatog.* 60, 167–177. The dye content of such a Delta Blue Agarose (DBA) matrix should, preferably, be 50±5 mmole/g dry weight.

Use of Blue Matrix. The method uses DBA at a bed height of 10–30 cm, preferably 20–30 cm (in this example 25 cm), with a column loading of 7–14 g rHA/l matrix, preferably 8–12g/l (in this example 10±1 g albumin/L matrix); all steps are run at a flow rate of 0.3–2.0 cm/min. preferably 1.0–2.0 cm/min, in this example 1.53 cm/mm. The DBA is equilibrated in CS01 from CS07; equilibration is complete when the pH of the column effluent is approximately pH9.5. Prior to chromatography, the SP-FF eluate is adjusted to approximately pH8.5–9.5, preferably pH 9.0, with ammonia, and then loaded onto the column. When loading is complete, the column is washed to remove contaminants with 1–5 volumes of buffer 10–30 mS cm$^{-1}$, preferably 15–25 mS cm$^{-2}$, for example CS12, preferably 5 column volumes. The albumin is eluted using a high ionic strength buffer of >100 mS cm$^{-1}$, preferably 125–165 mS cm$^{-1}$, for example CS03. Eluate collection is started when the UV signal ($A_{280}$/cm) rises above 0.4, and stops when the signal falls below 0.4 again. The column is then cleaned using CS04 and stored in CS07.

Intermediate Ultrafiltration. This step concentrates the albumin for gel permeation chromatography. A cellulose-type membrane (nominal molecular weight cut off less than or equivalent to 30.000, for example 10.000) in an ultrafiltration apparatus is used to concentrate DBA eluate to a retentate concentration of 20–120 g/L albumin. preferably 80–110 g /L. The membranes are treated, post-use, by flushing out residual protein with water, or CS03 or CS05 from Table 3, and cleaning with 0.1M sodium hydroxide. The membranes may then be stored in 20 mM sodium hydroxide.

Gel Permeation Chromatography. This step purifies the albumin with respect to yeast antigens (if the albumin is rHA from a yeast fermentation), pigment and dimerised albumin and performs a buffer exchange step. The method uses a commercial gel permeation matrix such as Sephadex G100, G150, G250, Sephacryl S-100, S-200 or S-300, Toyopearl HW50S or Superose 6 or 12. Preferably, the matrix is Sephacryl S-200 HR. (Pharmacia) at a bed height of greater than 60cm, preferably 90×cm (3×30 cm). The column is equilibrated in CS05 and run at 0.1–1.5 cm/min, preferably 0.5–1.0 cm/min, in this example 0.75 cm/min; the column is then loaded with albumin from the intermediate UF step when pH 9.5 is reached. The load volume is equivalent to approximately 2–9% of the column volume, preferably 5–8%, for example 7.5% of the column volume. The albumin fraction is collected in three parts: an initial small amount of albumin dimer goes to waste until the $A_{280}$ s/cm reaches 10% full scale deflection (FSD) on the way up; at this point collection of a recycle fraction starts and continues until 90% FSD and then the albumin is collected as the primary product fraction. This continues until the A,80 falls through 5% FSD, after which the effluent stream is directed to waste a gain. The recycle and primary product fractions are collected separately. This step is repeated until all the material has been loaded onto the column.

S-200 HR Recycle Ultrafiltration. A cellulosic type membrane, nominal molecular weight cut-off equal to or less than 30.000. or as used in this example 10.000. in an ultrafiltration apparatus, is used to concentrate the pooled recycle fraction to a retentate concentration of 20–120 g/L albumin, preferably 80–110 g/L. The membranes are treated post-use as described above under Intermediate Ultrafiltration.

Alternatively, as in any ultrafiltration steps in this process, polyethersulfone or PVDF membranes with a cut-off of ≤30,000 may be used instead of the cellulose-type membranes. Such membranes are available from Amicon and Millipore. It is preferable to use membranes which are compatible with NaOH. used for storage and cleansing of the membranes.

Purification of S-200 HR Recycle Ultrafiltration Retentate. The retentate from recycle ultrafiltration is loaded onto the same column as used for the primary S-200 purification and a product fraction collected from each peak, which is then mixed with the bulked primary product fractions collected previously. This step is repeated until all the material has been loaded onto the column.

Anion Exchange Chromatography. The aim of this step is to purify albumin with respect to at least yeast antigens (if the albumin is rHA from a yeast fermentation) and pigmented albumin. The method uses an anion exchange matrix such as QMA-Spherosil, DEAE-Spherodex, Q-Hyper D, DEAE-cellulose, QAE-cellulose, or TMAE, DMAE, or DEAE Fractogel. Preferably, the matrix is the commercial anion exchange matrix DEAE Sepharose-FF (Pharmacia) at any convenient bed height in the range 5–25cm, preferably 10–15 cm, for example 12.5cm, with a column loading of 10–60 g albumin per litre of matrix, preferably 35±15 g/L matrix. The column is first equilibrated in a strong buffer to bring the pH down to the working range quickly, eg sodium acetate pH 4.5–6.0. preferably approximately pH5.5, for example CS11. After the concentrated buffer, a solution of lower conductivity, namely in the range 1–4 mS cm$^{-1}$, preferably 2.5–3.5 mS cm$^{-1}$, for example CS08, is used to equilibrate the column prior to loading the column with S200 eluate. A linear flow rate of 1.0–8.0 cm/min, preferably 3.0–7.0 cm/min. in this example 4.4 cm min$^{-1}$, can be used. When loading is complete, the column is washed with a solution of sodium tetraborate in the range 5–30 mM, preferably 15–25 mM, for example CS10. This causes any carbohydrate-containing contaminants to adhere to the column more strongly prior to elution of the albumin fraction. Elution can be effected by any high ionic strength solution in the range 10–20 mScm$^{-1}$, preferably with CS06. The eluate is collected when the A$_{280}$/cm reaches 0.4, and continues until the peak falls through 0.8.

Hence, in this example, the sequence of purification steps is: cation exchange, affinity chromatography, ultrafiltration, gel permeation (with ultrafiltration of recycle fraction) and anion exchange.

The eluate from the DE-FF column has been found to have less than 0.1 % (w/w) albumin dimer and an undetectable level of albumin polymers or aggregates as analysed by GP HPLC using a TSK SW3000 XL column, loaded with 25.0 μl of eluate containing 10.0 mg/ml of albumin.

EXAMPLE 3

Formulation of Purified Albumin into a Final Product

This Example illustrates the concentration, diafiltration and formulation of the highly purified albumin into a suitable product, in this instance 25%(w/v) albumin. This procedure is carried out in two stages, namely final ultrafiltration (UF) and formulation. Final UF begins with transfer of the DEAE eluate (adjusted to pH 7.0×0.3 with phosphoric acid) to the: Final UF feed vessel and terminates after retentate and washings, if any, are transferred to the formulation vessel. The albumin-containing process stream is sequentially subjected to primary concentration, diafiltration and secondary concentration in an ultrafiltration system fitted with cellulosic or, more preferably, polyethersulphone membranes with a nominal molecular weight cut off limit of 10,000. The initial concentration step increases the albumin concentration to approximately 100 g.L$^{-1}$ and is immediately followed by the continuous diafiltration phase where the albumin is diafiltered against at least 5, preferably at least 7, retentate volume equivalents of water-for-injection.

In some purification processes of the invention, for example the step set out in Example 7 using immobilised aminophenylboronate, ammonium ions may be present at this stage. Surprisingly, we have found that these ammonium ions are bound quite tightly by the albumin and cannot be completely removed by diafiltration against water. We have found that diafiltration against a salt solution is effective. A ratio of 0.5 to 10% w/w of sodium chloride to albumin, for example 1.0 to 5.0% or about 3%, may be used. The salt may be added to the albumin retentate or, more usually, will be added to the diafiltration water. For an ultimate 5% (w/v) formulation, a solution of approx 100 g/l may be recovered directly from the diafiltration step. For an ultimate 25% (w/v) formulation, a solution of approx 275–325 g/l is obtained following a further concentration step (UF). Finally, the solution is transferred to the bulk product formulation vessel.

The formulation step produces albumin in an appropriate chemical environment and at an appropriate concentration suitable for bulk product sterile filtration (0.22 μm hydrophilic polyvinylidene-difluoride) and filling. The transferred solution is analysed to determine concentrations of albumin, sodium and octanoate. These quantities are taken into account and any necessary further amounts of stock sodium chloride and sodium octanoate excipient solutions and appropriate grade water added to achieve the bulk formulation specification. The final albumin concentration may be 235–265g.L$^{-1}$ (ie about 25%), with a sodium concentration of 130–160 mM. Any other feasible albumin concentration may be made, however, with, for example, a minimum concentration of at least 4% (w/v), preferably 4–25% (w/v). Formulation is complete following addition of appropriate conventional pharmaceutically acceptable excipients, such as those specified in the US or European Pharmacopoeias for human albumin, and diluting water.

A final concentration of 0.08 mmoles sodium octanoate per gram of albumin may be desirable. The product is sterile and non-pyrogenic. There may be about I % (wiw) dimeric albumin but no larger polymers or aggregates are detectable as analysed by GP HPLC using a TSK SW3000 XL column.

EXAMPLE 4

Cation Exchange Followed Directly by Anion Exchange

In a variation of the process of Example 2, the order of the steps was altered and some changes were made in the process conditions. A further table of chromatographic solutions is therefore provided, as Table 3. In addition, all of the chromatographic columns except the gel permeation step are radial flow.

TABLE 3

CHROMATOGRAPHY SOLUTIONS FOR EXAMPLE 4

| Solution | | | Concentration | | |
|---|---|---|---|---|---|
| No. | Name | Constituent | (g.L$^{-1}$) | pH | (mS.cm$^{-1}$) |
| CS20 | SP-FF Equilibrant/Wash/ DE-FF Equilibrant | CH$_3$COOH<br>NaOH (27% (w/w)) | 1.85<br>4.00 | 5.45–5.65 | 1.9–2.2 |
| CS23 | SP-FF Eluent<br>DE-FF Pre-Equilibrant | CH$_3$COOH<br>NaOH (27% (w/w))<br>Octanoic Acid | 5.13<br>11.5<br>0.721 | 5.4–5.6 | 5.0–6.0 |
| CS24 | SP-FF/DE-FF Salt Clean | NaCl<br>Tween 80 | 58.4<br>5.00 | 5–9 | 75–95 |
| CS25 | 0.5 M NaOH (UF membrane clean) | NaOH (27% (w/w)) | 74.1 | >12 | 80–120 |
| CS26 | 20 mM NaOH | NaOH (27% (w/w)) | 2.96 | >12 | 3.5–5.5 |
| CS27 | DE-FF Wash | K$_2$B$_4$O$_7$.4H$_2$O | 4.80 | 9.0–9.4 | 2.5–3.5 |
| CS29 | DBA Equilibrant/Wash | CH$_3$COONH$_4$<br>NaOH (27% (w/w)) | 19.3<br>5.93 | 8.7–9.1 | 18–22 |

TABLE 3-continued

CHROMATOGRAPHY SOLUTIONS FOR EXAMPLE 4

| Solution | | Concentration | | |
|---|---|---|---|---|
| No. Name | Constituent | (g.L$^{-1}$) | pH | (mS.cm$^{-1}$) |
| CS30 DBA Eluent | NaCl | 117 | 6.7–7.1 | 125–165 |
| | NaOH (27% (w/w)) | 14.1 | | |
| | H$_3$PO$_4$ (85 % (w/w)) | 5.79 | | |
| CS32 0.1 M NaOH (UF membrane storage) | NaOH (27% (w/w)) | 14.8 | >12 | 16–24 |
| CS33 2 M Sodium Octanoate | NaOH (27% (w/w)) | 281 | 7.8–8.4 | — |
| | Octanoic Acid | 288 | | |
| CS34 Acetic Acid | CH$_3$COOH | 1045 | — | — |
| CS35 0.5 M Phosphoric Acid | H$_3$PO$_4$ (85% (w/w)) | 59.0 | <1 | — |

All weight tolerances to ±0.5%.

The initial cation exchanger step was essentially the same as in Example 2, but with the following variations. The bed flow path length was 11.0±1.0 cm. The chromatography was then carried out as follows.

An SP-FF (Pharmacia) column was equilibrated in four volumes of 10–100 mM acetate, preferably 20–40 mM, for example 30 mM as in CS20, and the albumin solution was loaded at a flow rate of 0.07 to 0.75 bed volumes per min, preferably 0.3–0.6, in this example 0.5 bed volumes per minute. The column was washed with eight volumes of 10–100 mM, preferably 30–70, for example 50 mM acetate (CS21) and then ten volumes of CS20 and the albumin eluted with, and collected in an acetate/octanoate buffer (for example 40–120, preferably 60–100, eg 85 mM acetate, and 2–50, preferably 2–20, eg 5 mM octanoate, as in CS23) using an A$_{254}$/cm of 0.6 and 0.36 to mark the start and end of collection. The column is cleaned with 0.25–3.0 M salt and 0.05–2% detergent (CS24) and then 0.1–1.0 M caustic (CS25)° and stored in dilute (10–50 mM) caustic (CS26). In this example, the flow rate for the equilibration, loading and washing steps is 0.5 bed volumes per minute. For elution of the albumin, a flow rate of 0.04–0.6 bed vol/min, preferably 0.15–0.35, in this example 0.25 bed vol/min is used. The anticipated recovery of rHA monomer is between 46 and 66%.

The albumin was therefore eluted from the cation exchange column with a solution of octanoate, achieving a novel biospecific elution of rHA from a cation exchanger. The pH is close to the pI of the albumin so that the binding of the octanoate causes a significant overall charge difference; for example, the pH is at least 4.5, preferably about pH 5.5.

The eluate from the cation exchanger is then loaded directly (ie instead of after affinity and gel permeation chromatography as in Example 2, but preferably after dilution) onto the anion exchange resin at a pH of 4.5–6.5, preferably about 5.5, and a conductivity preferably in the range 1.5 to 5.0 mS.cm$^{-1}$, for example 2.5±0.5 mS.cm$^{-1}$. This has been found to result in any dimeric albumin that was formed during the cation exchange chromatography being converted back to monomeric albumin under the conditions of the anion exchange chromatography. A yield of approximately 110% for albumin monomer has been achieved over this step.

In more detail, an 11.0±1.0 cm bed flow path length column of DEAE-Sepharose Fast Flow (Pharmacia) is pre-equilibrated with the cation exchange elution buffer (CS23) and then equilibrated with an acetate buffer (for example CS20) before being loaded with 30.0±10.0 g monomeric albumin per litre of matrix.

The column is then washed with a borate solution as in Example 2 (CS27), eluted as in Example 2 (CS06), and cleaned with salt/detergent (CS24), caustic (CS25) and stored in dilute caustic (CS26) all as for the cation exchange column. The flow rate for all the steps is 0.07 to 0.75 bed vol/min, preferably 0.3–0.6, in this example 0.5 bed volumes per minute.

The eluate from the anion exchange resin (eg DE-FF) still contains impurities and is then applied directly to the affinity matrix (eg Delta Blue Agarose as described in Example 2). The bed height was reduced from 25 cm in Example 2 to 11.0±1.0 cm which allowed a higher flow rate within normal operating pressure. Therefore, a bed height of 11.0 cm was preferred and does not adversely affect recovery of albumin or albumin purity. The column was equilibrated in ammonium acetate (100–300 mM, preferably 200–275, for example 250 mM as in CS29) and the albumin was applied at 7.0–14.0 g/l, preferably 8.0–12.0 g/l, in this example 10.0±1.0 g per litre of matrix. Equilibration, load and wash steps were performed at flow rates of 0.05–0.30 bed vol/min, preferably 0.15–0.27. in this example 0.25 bed vol/min. All other steps were performed at 0.04–0.30, preferably 0.1–0.25, and in this example. 0.20 bed vol/min. The increased flow-rate. facilitated by the reduced bed height. improved the throughput by a factor of four which is advantageous to the large scale plant design and was close to the maximum operating capability of the DBA. Since this increased flow rate did not appear to adversely affect recovery of albumin or albumin purity, it is preferred to utilise such a higher flow rate.

The column was washed with 5 column volumes of the ammonium acetate buffer (CS29), and the albumin was eluted with strong salt and phosphate solution (1.0–3.0 M NaCl, for example 1.5–2.5 M or 2.0 M NaCl. and 5–100 mM, eg 50 mM phosphate, as in CS30).

The pH of the eluant in this variant of the process was changed to pH7.0 from pH9.2. The buffer was changed accordingly from 50 mM ammonium acetate to 50 mM sodium phosphate which was preferred because of its buffering at pH7.0, and its relative cost. The lower pH eluant was responsible for an increase in DBA eluate albumin monomer recovery. A pH lower than 7.0 increased the fragment levels, and above pH7.0 the albumin monomer recovery was reduced. The pH, which can be in the range 5.5–9.0. is therefore preferably pH7.0. The column was cleaned and stored in caustic (CS25, CS26) as above.

The DBA eluate (optionally after ultrafiltration with a cellulosic type membrane (nominal cut off MW30,000) to give 80–110 g/l of albumin) was then applied to the gel permeation resin, for example S-200 (HR). The S-200 running bluffer was changed to 40 mM sodium phosphate pH7.0. The sodium octanoate was omitted from this buffer for cost reasons, and instead was added to the solution prior to diafiltration (added to a concentration of 1–20 mM, preferably 5mM). The phosphate conferred a higher conductivity on the running buffer which improved the purity. A high salt concentration can be used to increase conductivity but it is still preferable to buffer the solution. The pH7.0 was preferable since this was the desired pH for formulation.

Hence, in this example, the sequence of purification steps is: cation exchange (eluting with a molecule specifically bound by albumin), anion exchange, affinity chromatography and gel permeation.

The diafiltration step prior to formulation may be assisted by starting with albumin at pH7.0. The albumin was more concentrated at the final eluate than with the process of Example 2, assisting the final ultrafiltration step prior to formulation (Example 3).

EXAMPLE 5

High Salt Wash on Cation Exchanger

In a further variation of the process, the process of Example 2 or 4 was followed except as follows. Following loading of the albumin on to the cation exchange column (for example SP-Sepharose FF, Pharmacia), the column was washed with CS21 (50 mM sodium acetate, pH 3.9–4.1, 0.6–0.8 mS.cm$^{31}$ $^1$), then further washed with a high salt buffer containing 1–3M NaCl, preferably 2M NaCl, in sodium acetate buffer (for example 10–5 mM sodium acetate, preferably about 27 mM, pH 3.5–4.5, preferably pH4.0) before the final wash in CS20. This more stringent washing procedure results in an eluate containing a lower level of non-albumin proteins and may be especially useful if the albumin is rHA from a yeast fermentation. The albumin was eluted as described in Example 4. The lowering of the pH prior to the high salt wash helps to retain the albumin on the column during that wash, and the final wash also maximises albumin recovery. It is probable that neither step has a major effect on the purity of the albumin recovered.

EXAMPLE 6

Concentrated Borate Elution from Anion Exchanger

In this example, the process of Example 2 or 4 (with or without the variation in Example 5) was varied as follows. The eluate from the cation exchange column was diluted to below 10 mS.cm$^{-1}$, preferably less than 5 mS.cm$^{-1}$, and then loaded on to an anion exchange matrix (for example DEAE Sepharose FF, Pharmacia). The anion exchange matrix was then washed with dilute tetraborate buffer (for example 15–25 mM potassium tetraborate or sodium tetraborate), which has the effect of raising the pH to approximately 9.2, and then the albumin was eluted with a more concentrated tetraborate buffer (for example 80–150 mM potassium tetraborate, preferably 110 mM potassium tetraborate). In Examples 2 and 4, the albumin was eluted with 20 mM tetraborate, 100 mM NaCl; elution with 80–150 mM tetraborate (eg 33.6 g/l) results in an eluate with a lower content of carbohydrate-containing contaminants, for example yeast glycoproteins, due to an increased affinity of these species for the anion exchange matrix under these conditions. Potassium tetraborate is used in preference to sodium tetraborate because of its higher solubility at room temperature. The eluate from the anion exchange matrix was dealt with as in Example 2 or 4. For example, in the Example 4 process, it was then directly loaded onto an affinity matrix, eg Delta Blue Agarose (DBA), which was run as described in Example 4.

A gel permeation step is then carried out as in Example 2 or 4.

EXAMPLE 7

Immobilised Aminophenylboronate

The eluate from the DBA matrix may be applied to a gel permeation medium, for example Sephacryl S-200 (HR) (Pharmacia), equilibrated in an ammonium acetate buffer (for example 10–100 mM, preferably about 30 mM), containing sodium chloride (20–2000 mM, preferably about 100 mM) and octanoate (1–20 mM, preferably about 5 mM octanoate at pH 9.0–9.5. preferably 9.2). This buffer effectively exchanges the albumin into a suitable solution for the final chromatographic step, set out in more detail below.

The S-200 step is run as follows. The S-200 is run at a minimum bed height of 90.0 ±3 cm (eg 3×30 cm in series). (a) The retentate from intermediate ultrafiltration is loaded onto the column. Recycle and product fractions are collected. This step is repeated until all the material has been loaded onto the column. (b) The pooled recycle fractions are concentrated to 80–110 g rHA/L by ultrafiltration as above. (c) The retentate from recycle ultrafiltration is loaded onto the same column and a product fraction collected from each peak. This step is repeated until all the material has been loaded onto the column. (d) The product fractions from the primary and secondary gel permeation chromatography steps ((a) and (c)) are pooled as the S-200 eluate.

The final step consists of an affinity step to remove glycoconjugates such as glycoproteins and glycolipids, and poly—, oligo— and monosaccharides. This step uses immobilised aminophenylboronic acid (PBA) as the ligand, U.S. Pat. No. 4,562,251 (incorporated herein by reference) describes suitable methods for making diborotriazine agarose or monoborotriazine agarose: (1) Triazine is 0-linked to agarose first and then linked with 3-aminophenylboronic acid (APBA) in a second reaction. If the X on the triazine is replaced with chlorine then the disubstituted resin t is produced. (2) Triazine is reacted with APBA first to produce either mono or diborotriazine. These are then O-linked via the free chlorine on the triazine to the —ONa activated agarose to produce either mono or disubstituted agarose. All of the examples and descriptions in this patent use —ONa activated agarose which results in O-linkages.

An earlier U.S. Pat. No. 4.269,605 contemplates a variety of matrix activation methods. including epichlorohydrin activation of agarose. preferred herein. Commercially available matrices include Amicon's PBA30 and Sigma's acrylic beaded aminophenylboronate.

The albumin collected from the S-200 column was chromatographed through the PBA matrix, having been pre-equilibrated in S-200 running buffer (see above): under these conditions, the albumin does not bind appreciably to the matrix, whereas the carbohydrate-based contaminants are retarded sufficiently to separate them from the albumin as it passes through the column. The chromatography is thus in the negative mode with respect to the albumin. Further details were as follows:

The phenyl boronate matrix had a flow path length of 11.0±1.0 cm and was equilibrated with a buffer containing ammonium ions (10–50 mM), acetate (10–50 mM) and 1.0–10.0 mM octanoate (eg CS36 - see table below). The column was then loaded at 35±15 g of rHA/L matrix. The PBA is run as a negative step and therefore the product collected is the flow through during loading and the subsequent wash with the equilibration buffer. All chromatographic steps can be performed at flow rates in the range 0.005–0.3 bed vol/min. Preferably equilibration and cleaning of the column are carried out at a higher flow rate, eg 0.19 bed vol/min, than load and collection of the albumin solution, which is preferably carried out at a flow rate of 0.01–0.05, preferably 0.025 bed vol/min. The column is then cleaned with a borate buffer (as in CS37), salt (CS38) and caustic (CS25) and then stored in the borate buffer (CS37).

The pH of the collected flow through and wash is adjusted to 7.0±0.1 with phosphoric acid solution (CS35).

The buffers used are as follows:

TABLE 4

Chromatography solutions for Example 7

| Solution | | | | | |
|---|---|---|---|---|---|
| No. | Name | Constituent | Concn (g/l) | pH | Conductivity (mS.cm$^{-1}$) |
| CS36 | PBA equilibration/ wash | CH$_3$COONH$_4$ NaOH (27% w/w) NaCl Octanoic acid | 2.31 2.55 5.84 0.721 | 9.0–9.4 | 12.0–15.0 |
| CS37 | Borate Clean | K$_2$B$_4$O$_7$.4H$_2$O | 33.6 | 9.2–9.5 | 15.0–18.0 |
| CS38 | Salt clean | CH$_3$COOH NaOH (27% w/w) NaCl | 1.62 1.19 117.0 | 3.9–4.1 | 125.0–165.0 |

Because of the use of ammonium ions in the PBA buffer, it is advantageous to use salt in the final ultrafiltration step, as explained in Example 3 above.

In a particularly preferred process, the sequence of steps is as follows:

(1) Yeast fermentation as in Example 1.

(2) Centrate conditioning as in Example 2.

(3) Cation exchange (SP-FF) with high salt wash, as in Example 5. and elution with albumin-specific compound, as in Example 4.

(4) Dilution and anion exchange with concentrated tetraborate elution as in Example 6.

(5) Affinity chromatography (DBA) as in Example 4.

(6) Intermediate ultrafiltration and then gel permeation (S-200), with recycle ultrafiltration, as in Example 7.

(7) Chromatography on immobilised borate as in Example 7.

(8) Final ultrafiltration and formulation as in Example 3.

EXAMPLE 8

Earlier Use of Immobilised Phenylboronate

The step involving immobilised phenylboronate may be used earlier in the process, for instance in a process in which the steps are ordered: cation exchanger—anion exchanger—affinity material—ultrafiltration/diafiltration—immobilised phenylboronate—gel permeation.

The conditions for each step are as in Examples 4 to 7, except as follows. The DBA eluate is concentrated to 80–110 g/l albumin and the pH is adjusted to 9.2 by diafiltering (5 volumes) against an ammonium acetate of the kind used in Example 7. The concentrated DBA eluate is then chromatographed on PBA and the flowthrough is collected and applied directly to the gel permeation (eg S200) column. As the gel permeation step is now the last step, it may run in a buffer which is suited to the formulation step, for example 20–130 mM (preferably 50–100 mM) NaCl, at pH 7.0.

EXAMPLE 9

Characterisation of the Albumin Produced According to the Invention

This Example illustrates the analysis that is carried out to establish the purity of albumin purified in accordance with the present invention. Unless stated otherwise, all of the assays are performed on albumin which has been formulated as described in Example 3 to yield the final product.

Glycation of rHA

A microassay for glycated protein has shown that (rHA) purified in accordance with the invention is not modified by non-enzymic glycosylation (glycation). The microassay measures the stable Amadori product (AP) form of glycated protein. by oxidation of the C-1 hydroxyl groups of AP with periodate. The formaldehyde released by periodate oxidation is quantitated by conversion to a chromophore, diacetyldihydrolutidine (DDL), by reaction with acetylacetone in ammonia. DDL is then detected colorimetrically at 405 nm.

| Albumin batch | Mole hexose/mole protein |
|---|---|
| A | 0.092 |
| B | 0.116 |
| C | 0.090 |
| D | 0.132 |
| E | 0.060 |
| G | 0.04 |
| H | 0.01 |
| I | 0.07 |
| J | 0.07 |
| K | 0.05 |
| L | 0.740 |
| M | 0.70 |
| N | 0.96 |
| O | 0.78 |

Batches A-K were rHA purified according to Example 2. Batches L-O were samples of commercially available human serum albumin from differing sources. Eight batches of rHA purified according to Example 7 had a negligible level of glycation (0.042±0.018 moles/mole) compared to HSA (0.387±0.012).

Low Molecular Weight Contaminant Assay

Rationale—The aim of this assay is to remove non-covalently bound low molecular weight contaminants (LMC) from rHA and HSA using acidic organic solvents. An HPLC "fingerprint" chromatogram can then be produced for comparison of samples.

Method—To 100 µl of final product (20 mg; rHA or HSA) is added sequentially 50 µl formic acid (98% v/v), 100 µl chloroform and 50 µl ethanol with vortexing after each addition. The samples are kept at room temperature for 5 mins with regular mixing. Protein is then precipitated by the addition of 1 ml acetone (30 mins, −20° C.). The protein samples are pelleted by centrifugation and the supernatants are decanted off and dried by rotary evaporation under vacuum. The dried samples are resuspended in 25% acetonitrile/0.1% trifluoroacetic acid. LMCs are then separated on an ABI PTH C18 reverse phase column (220×2.1 mm) using a linear 10%–90% acetonitrile gradient in 0.1 % trifluoroacetic acid (flow rate=300 µl/min). The samples were monitored at 214nm using a Shimadzu UV monitor.

Figure 2:
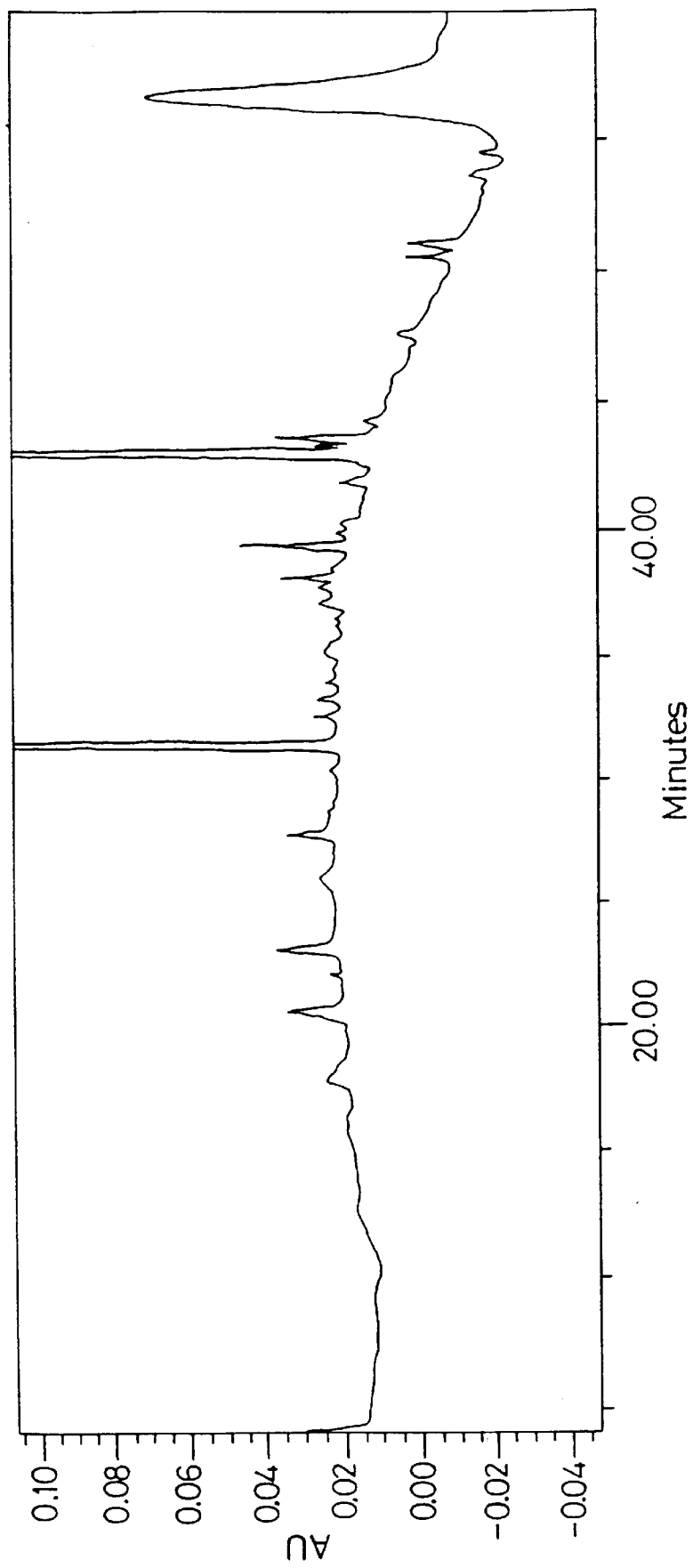
FIG. 2 is a UV trace from a C18 PTH Reverse Phase HPLC column (Applied Biosystems Inc), showing the low level of low molecular weight contaminants in the albumin of the invention.

Results—A comparison was made between a commercially available batch of human serum albumin and a batch of rHA purified according to the invention. Two main significant $A_{214nm}$, peaks are seen in the sample of the invention ($R_1$=31.1 and 42.8 mins respectively—see FIG. 2 and Table 9). The peak at 2.15 mins is thought to be due to insoluble or partially soluble material passing through the column. and the large peak at 56.5 mins is also present in the trace of a water blank and thus is regarded as an artefact.

TABLE 5

Peak Results

| # | Ret Time (min) | Area (uV.sec) | Height (uV) |
|---|---|---|---|
| 1 | 0.800 | 3459686 | 219122 |
| 2 | 1.667 | 418606 | 33569 |
| 3 | 2.150 | 77883335 | 1963630 |
| 4 | 3.000 | 6293258 | 122295 |
| 5 | 20.433 | 297608 | 14424 |
| 6 | 22.900 | 205822 | 14601 |
| 7 | 27.567 | 150851 | 10835 |
| 8 | 31.117 | 2213883 | 170938 |
| 9 | 37.983 | 164710 | 15088 |
| 10 | 39.267 | 347946 | 29879 |
| 11 | 41.750 | 107515 | 8402 |
| 12 | 42.783 | 2303024 | 192911 |
| 13 | 43.217 | 139744 | 14141 |
| 14 | 43.457 | 254521 | 23979 |
| 15 | 50.467 | 152805 | 13226 |
| 16 | 50.950 | 162364 | 12577 |
| 17 | 56.533 | 5753796 | 83674 |

Figure 3:
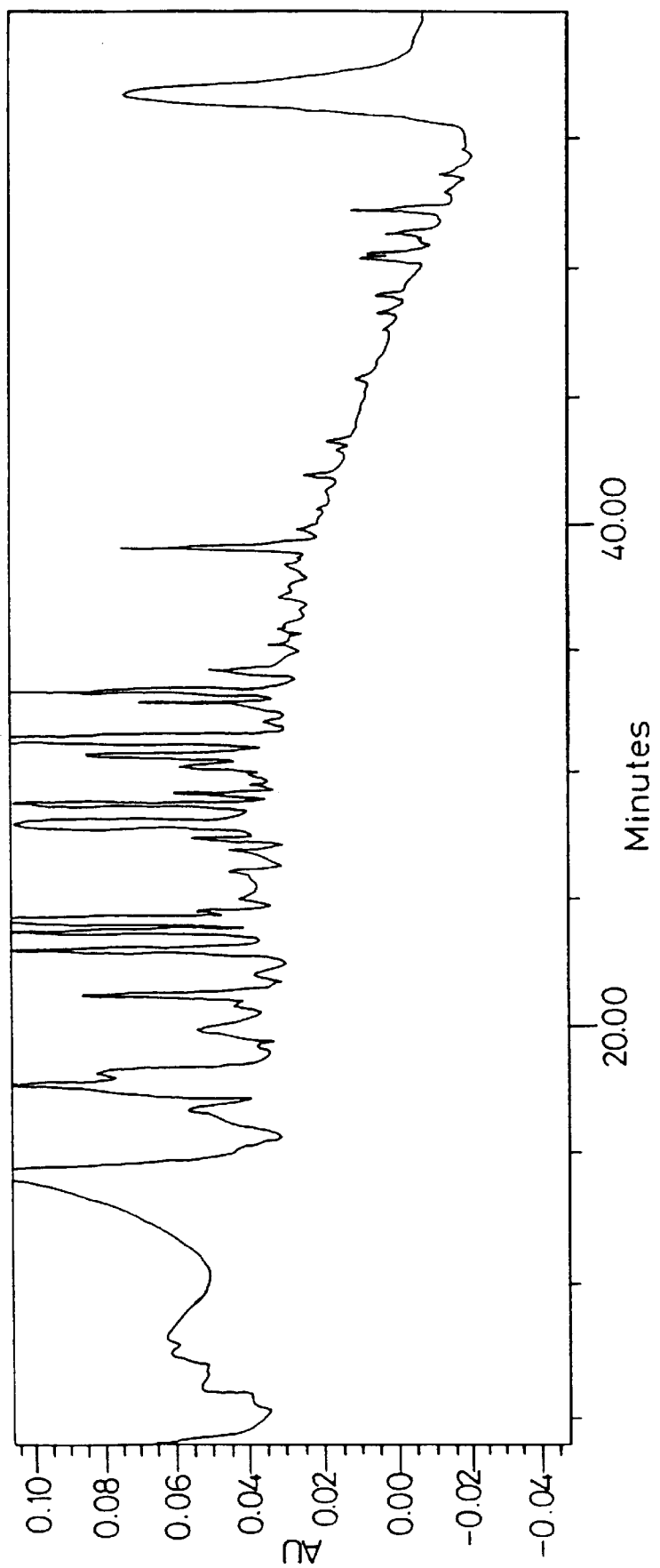
FIG. 3 is similar to FIG. 2 but shows low molecular weight contaminants in prior art albumin.

The commercially available HSA, on the other hand, has many more peaks (see FIG. 3 and Table 6).

TABLE 6

Peak Results

| # | Ret Time (min) | Area (uV.sec) | Height (uV) |
|---|---|---|---|
| 1 | 0.350 | 244385 | 23957 |
| 2 | 0.633 | 607880 | 45310 |
| 3 | 0.783 | 3239730 | 243477 |
| 4 | 0.983 | 1072033 | 158146 |
| 5 | 2.233 | 76773569 | 2038028 |
| 6 | 2.933 | 6634089 | 182363 |
| 7 | 3.733 | 2812688 | 95459 |
| 8 | 12.483 | 818540 | 20185 |
| 9 | 12.650 | 218748 | 22750 |
| 10 | 14.150 | 5423715 | 98336 |
| 11 | 16.333 | 423403 | 17460 |
| 12 | 16.633 | 688525 | 24538 |
| 13 | 17.550 | 2301309 | 84781 |
| 14 | 18.033 | 1145045 | 47806 |
| 15 | 19.750 | 672721 | 21562 |
| 16 | 20.233 | 87799 | 9760 |
| 17 | 20.700 | 272171 | 13003 |
| 18 | 21.100 | 862146 | 55792 |
| 19 | 21.967 | 166471 | 8928 |
| 20 | 22.883 | 1381445 | 97660 |
| 21 | 23.583 | 1112632 | 89851 |
| 22 | 24.000 | 4740347 | 419780 |
| 23 | 24.417 | 352486 | 26374 |
| 24 | 24.917 | 171279 | 14625 |
| 25 | 25.133 | 99734 | 11473 |
| 26 | 25.267 | 133911 | 10515 |
| 27 | 25.667 | 223556 | 11854 |

TABLE 6-continued

Peak Results

| # | Ret Time (min) | Area (uV.sec) | Height (uV) |
|---|---|---|---|
| 28 | 25.967 | 257295 | 17351 |
| 29 | 26.600 | 93906 | 7957 |
| 30 | 26.817 | 223113 | 18326 |
| 31 | 27.250 | 303831 | 29461 |
| 32 | 27.533 | 124218 | 12710 |
| 33 | 27.783 | 5747091 | 561629 |
| 34 | 28.550 | 1383761 | 119772 |
| 35 | 29.033 | 390986 | 33455 |
| 36 | 29.417 | 182131 | 12713 |
| 37 | 29.833 | 181333 | 12584 |
| 38 | 30.183 | 478320 | 30155 |
| 39 | 30.583 | 1048945 | 58465 |
| 40 | 31.067 | 3454425 | 214489 |
| 41 | 31.983 | 168275 | 8663 |
| 42 | 32.717 | 651406 | 43161 |
| 43 | 33.150 | 1142221 | 102588 |
| 44 | 34.017 | 420756 | 23883 |
| 45 | 35.100 | 115704 | 10008 |
| 46 | 37.033 | 166588 | 9468 |
| 47 | 38.267 | 145731 | 8078 |
| 48 | 38.983 | 781209 | 54029 |
| 49 | 41.800 | 86967 | 8868 |
| 50 | 48.883 | 95416 | 8522 |
| 51 | 50.267 | 174159 | 16737 |
| 52 | 50.483 | 176115 | 15573 |
| 53 | 51.267 | 158727 | 13701 |
| 54 | 52.183 | 297278 | 25795 |
| 55 | 56.533 | 5846645 | 85710 |

The quality of the albumin of the invention in terms of non-covalently bound LMCs is clearly superior to that of clinical HSA. Expressed numerically, the total peak area between 10 mins and 55 mins for the albumin of the invention was about 6.4 V.sec whereas the total peak area between the same two times for commercially available material was about 39.7 V.sec.

A similar analysis was carried out with detection at 280 nm, in which case the peak area for albumin purified according to the invention was 0.56 V.sec. whereas that for HSA was 14.9 V.sec.

Analysis of fluorescent low molecular weight contaminants (excitation at 280 nm, detection at 350 nm) again revealed a total peak area for albumin purified by the process of the invention of less than 10% of that for HSA.

Capillary Zone Electrophoresis of rHA and HSA

Capillary electrophoresis (CE) is used as an alternative to standard SDS-PAGE in order to qualitatively compare purified rHA of the invention and commercially available HSA. CE is a high resolving electrophoretic technique and is capable of separating sub-populations of the same protein when only minor differences are to be found.

Method—Samples of HSA (Armour) and rHA purified according to the invention were separated in 20 mM $PO_4$/$B_4O_7$ buffer, pH=7.4 at 20 KeV and 30° C. were electrophoresed on an ABI 270 CE. The rHA of the invention gave a single peak on the electrophoretogram indicative of its homogeneity. In contrast, other peaks were observed in the commercially available HSA samples. These peaks are believed to be indicative of the presence of albumin molecules with, for example, blocked free thiol groups or amino terminal degradation.

Analysis of C-terminus

An important aspect of the quality control of recombinant proteins is the confirmation and stability of the predetermined primary structure.

Materials and Methods

Tryptic Digestion: HSA (from a commercial source—one sample stored at −20° C. and one stored at 30° C. for 12 weeks), rHA purified according to the invention (stored at 4° C. and 30° C. for 6 months) and a Des-Leu rHA (a truncated form of rHA minus the C-terminal leucine) (1 mg each) were reduced with 5 mM dithiothreitol (Calbiochem) for 120 min 37° C., then alkylated with 10 mM iodoacetamide (Sigma) for 90 mins at 37° C. in 6M guanidine HCl in 0.5M Tris HCl pH 8.0.

The samples were then diluted 1 in 3 with $H_2O$ and digested with trypsin for 48 hours at 37° C. (TPCK treated trypsin from Sigma, 3×10 µl aliquots of 1 mg/ml solution added over 48 hours).

Peptide Mapping: Tryptic digests were mapped on reverse phase (RP) HPLC on a Gilson HPLC system using a 25 cm Pharmacia SuperPac PepS column (5 µm $C_2/C_{18}$. The eluents used were A, 0.1% (v/v) TFA (ABI) in water; B, 0.09% (v/v) TFA in 70% (v/v) acetonitrile (Fisons Scientific)— linear gradient over 60 min, 0.5 ml/min. UV detection at 214 nm and 280 nm.

N-terminal Sequencing: Performed on an ABI 477A protein sequencer.

Fast Atom Bombardment—Mass Spectrometry: FAB-MS was performed on a VG Autospec by M-Scan Limited, Ascot, UK.

Peptide Synthesis: The full length C-terminal tryptic peptide LVAASQAALGL (SEQ. ID. NO.:1) (mass 1012) was synthesised by ABI, Warrington. UK; and the truncated version LVAASQAALG (SEQ. ID. NO.:2) (mass 899) was synthesised by the Department of Biochemistry, University of Nottingham, Nottingham, UK.

Results

The full length C-terminal tryptic peptide (mass 1012) was shown, using the synthetic marker peptide, to elute at 37.5 minutes on RP-HPLC. This peak was collected and identified by N-terminal Sequencing and FAB-MS from HSA and rHA.

Removal of the C-terminal leucine results in a truncated C-terminal peptide (mass 899) which was shown to elute at 28.5 minutes, confirmed using the synthetic marker peptide. This peak was isolated from the tryptic digest of Des-Leu rHA and identified by N-terminal Sequencing and FAB-Ms Two other peptides were, shown to be present in this 28.5 minute peak, AWAVAR (SEQ. ID. NO.:3) (mass 673) and DLGEENFK (SEQ. ID. NO.:4) (mass 950).

The 28.5 minute peak was collected off RP-HPLC from the tryptic digests of HSA, HSA stored at 30° C. for 12 weeks, Des-Leu rHA. rHA of the invention stored at 4° C. for 6 months and rHA of the invention stored at 30° C. for 6 months.

The peak from each digest was subsequently analysed by N-terminal Sequencing and FAB-MS along with the synthetic marker peptides.

TABLE 7

Peptides Present in 28.5 Minute Peak by N-terminal Sequencing.

| SAMPLE | SEQUENCE |
|---|---|
| Des-Leu rHA | LVAASQAALG (SEQ. ID. NO.: 2) |
|  | AWAVAR (SEQ. ID. NO.: 3) |
|  | DLGEENFK (SEQ ID. NO.: 4) |
| HSA standard | AWAVAR (SEQ. ID. NO.: 3) |
|  | DLGEENFK (SEQ. ID. NO.: 4) + |
|  | about 5% LVAASQAALG (SEQ. ID. NO.: 2) |

TABLE 7-continued

Peptides Present in 28.5 Minute Peak by N-terminal Sequencing.

| SAMPLE | SEQUENCE |
|---|---|
| HSA 30° C. 12 weeks | AWAVAR (SEQ. ID. NO.: 3) |
|  | DLGEENFK (SEQ. ID. NO.: 4) |
| rHA 4° C. 6 months | AWAVAR (SEQ. ID. NO.: 3) |
|  | DLGEENFK (SEQ. ID. NO.: 4) |
| rHA 30° C. 6 months | AWAVAR (SEQ. ID. NO.: 3) |
|  | DLGEENFK (SEQ. ID. NO.: 4) |

By FAB-MS, the main signals ((M+H)+molecular ions) present in the 28.5 minute peak were as shown in Table 8.

TABLE 8

$(M + H)^+$ Ions in 28.5 min Peak.

| | |
|---|---|
| Mixture of Synthetic Full Length and Truncated C-terminal Peptides | 1013- LVAASQAALGL (SEQ. ID. NO.: 1) |
|  | 900- LVAASQAALG (SEQ. ID. NO.: 2) |
| Des-Leu rHA | 673- AWAVAR (SEQ. ID. NO.: 3) |
|  | 900- LVAASQAALG (SEQ. ID. NO.: 2) |
|  | 951- DLGEENFK (SEQ. ID. NO.: 4) |
|  | 1028- ? |
|  | 1140- ? |
| HSA Standard | 673- AWAVAR (SEQ. ID. NO.: 3) |
|  | 900- LVAASQAALG (SEQ. ID. NO.: 2) |
|  | 951- DLGEENFK (SEQ. ID. NO.: 4) |
|  | 1028- ? |
|  | 1140- ? |
| rHA 30° C. 6 months | 673- AWAVAR (SEQ. ID. NO.: 3) |
|  | 900- LVAASQAALG (SEQ. ID. NO.: 2) |
|  | 1028- ? |
|  | 1140- ? |
|  | 951- No signal |

The signals at 1028 and 1140 may be fragment ions; they were not peptides that could be detected by sequence analysis.

Conclusion

The Des-Leu C-terminal tryptic peptide was detected in commercial HSA at approximately 5–10% (not quantitative), but could not be detected in the rHA of the invention, even after 6 months at 30° C. The Des-Leu peptide could not be detected in the HSA 12 weeks at 30° C., and the peak for the full length C-terminal peptide at 37.5 minutes (though not isolated) was very diminished compared to the other samples, indicating that perhaps this has undergone further C-terminal degradation.

These results indicate that the rHA, purified in accordance with the invention, has a stable and full length carboxy-terminus, whereas HSA previously available from commercial sources appears to be heterogeneous by comparison.

Colorimetric Assay for Free Thiols in Purified Human Albumin

Introduction—Ellmann's Reagent, 5,5'-dithiobis-(2-nitrobenzoate) (DTNB), is a specific and sensitive means of detecting free thiol groups such as Cys-SH. The reaction can be followed by monitoring absorbance at 412 nm, which value can be used to calculate free Cys-SH, to levels of less than one residue per molecule of rHA. The following solutions reagents are utilised in the assay:

5,5'-Dithiobis (2-nitrobenzoic acid) DTNB, Sigma Product No D8130. TRIS PRE-SET pH crystals pH8.0, Sigma Product No T4753. EDTA, disodium. Sigma Product No ED2SS. Sodium dihydrogen phosphate dihydrate, Analar grade. Disodium hydrogen phosphate dihydrate, Analar grade.

Buffer 1:0.1M (12.1 g) Tris-HCl; 0.01M (3.72 g) EDTA Na$_2$2H$_2$O, pH8.0. PRE-SET pH crystals. Dissolve in 500 ml water and make up to 1 litre exact volume. Stable for one month at room temperature.

Buffer 2:0.05M Sodium phosphate pH7.0. Na$_2$HPO$_4$2H$_2$O (5.45 g), 3.04 g NaH$_2$PO$_4$2H,O. Dissolve in 500 ml water, and make up to 1 litre exact volume. Stable for 1 month at room temperature.

Reagent: 0.01M (39.4 mg) DTNB in phosphate buffer. Dissolve in 10 ml buffer 2. Prepare fresh each day.

Sample: Dilute albumin to about 10.3 µM in buffer 1 (0.66 mg/ml).

Procedure

1) Set spectrophotometer cell holder thermostat to 25° C. 2) Place 1.25 ml of sample in one cuvette and 1.25 ml of buffer 1 in another 10 mm reduced volume cuvette in the sample and reference positions respectively. 3) Zero instrument at 412 nm. Set absorbance to 0.1 AU Full Scale. 4) Add 50 µl DTNB reagent to the reference cuvette, and mix briefly using a cleaned plastic stirrer. 5) Add 50 µl DTNB reagent to the sample cuvette, and mix as above. 6) Immediately start acquiring data (or start chart recorder, and follow reaction for up to 10 mins). 7) Repeat for each sample, to obtain values in triplicate. 8) Extrapolate back from the steady absorbance decay to zero time, and read off the absorbance at 412 nm ($\delta A_{412}$) (FIG. 1). 9) Calculate the sulphydryl content using the molar extinction coefficient $\epsilon_{412} = 13.9$ cm$^2$mM$^{-1}$.

Results

A number of commercial HSA samples were assayed for free thiol content. the results are summarised below:

| HSA | Free Thiol (mole SH/mole HSA) |
|---|---|
| 1 | 0.29 |
| 2 | 0.22 |
| 3 | 0.35 |
| 4 | 0.05 |
| 5 | 0.08 |
| 6 | 0.46 |
| 7 | 0.36 |

These values are significantly lower than the value for albumin prepared according to the example above which is routinely assayed at 0.85–0.9 mole SH/mole rHA.

The Determination of Metal Ion Contamination in Human Albumin by Graphite Furnace Spectroscopy Standards and samples are atomised from a pyrocoated graphite tube. The atomic absorption of the sample is detected using the following conditions:—

| Metal ion | Wavelength nm | Atomisation temperature ° C. |
|---|---|---|
| Zn | 213.9 | 1800 |
| Cu | 327.4 | 2300 |
| Fe | 248.8 | 2400 |
| Al | 309.8 | 2500 |
| Mn | 279.8 | 2200 |

Aluminium was measured using a Perkin Elmer M2100 atomic absorption spectrophotometer, a Perkin Elmer HGA-700 graphite furnace, a Perkin Elmer AS-70 Autosampler with sample cups and an aluminium hollow cathode lamp. The reagents were AR grade magnesium nitrate, an aluminium standard solution (1000 ppm) and AR grade concentrated nitric acid. A 1.00% w/v magnesium nitrate solution was made up with Milli-Q water. 15 µl of aluminium standard solution was pipetted into the autosampler and diluted to 1500 µl with 0.20% nitric acid solution. The procedure is repeated with 15 µl of the solution obtained and then with 150 µL of the solution subsequently obtained, to give a 10 ppb (µg/L) aluminium solution.

An albumin sample is diluted with 0.20% nitric acid solution to give an aluminium concentration within the limits of the calibration graph. A 1:2 dilution is usually sufficient.

Magnesium is measured similarly, using a Perkin Elmer AS-51 flame autosampler and a magnesium hollow cathode lamp. A Magnesium Standard solution of 1000 ppm is diluted with Milli-Q water to give 0.1, 0.2, 0.5 and 1.0 ppm standard solutions. The atomic absorption of the sample is detected at 285.2 nm.

Copper, iron, manganese and zinc are measured in the same way as aluminium except that, for zinc, a 1.0 ppb (µg/l) standard solution is used instead of a 10 ppb solution. The concentration of metal ions was determined in ng/L and then related to the concentration of albumin (ng metal ion/g albumin). These data are presented in Table 9.

TABLE 9

Contamination Profiles of Albumin produced according to the invention

Concentration in ng/g albumin

| Chemical | Batch A | Batch B | Batch C | Batch D | Batch E | Batch F | Batch G | Batch H | Batch I | Batch J | Batch K |
|---|---|---|---|---|---|---|---|---|---|---|---|
| Aluminium | — | 85 | — | — | — | — | — | 9 | 22 | 86 | 96 |
| Copper | 3720 | 9080 | 1780 | 660 | 2690 | 440 | 530 | 520 | 590 | 9920 | 8820 |
| Iron | 460 | 810 | 440 | 930 | 380 | 2720 | 1880 | 1010 | 670 | 1030 | 100 |
| Magnesium | 1200 | 850 | 800 | — | — | — | — | 600 | <400 | 2000 | 2000 |

TABLE 9-continued

Contamination Profiles of Albumin produced according to the invention

Concentration in ng/g albumin

| Chemical | Batch A | Batch B | Batch C | Batch D | Batch E | Batch F | Batch G | Batch H | Batch I | Batch J | Batch K |
|---|---|---|---|---|---|---|---|---|---|---|---|
| Zinc | 4510 | 1490 | 1790 | 1580 | 680 | 3520 | 2130 | 1740 | 1040 | 4280 | 3520 |
| Manganese | 20 | 191 | 16 | 42 | 14 | 58 | 27 | 35 | 20 | 46 | 60 |

All results are expressed as total metal ion concentration.

Table 10 shows the corresponding levels of metal ions in commercial HSA.

TABLE 10

Concentrations in ng metal/g of albumin

| Chemical | Source A (UK) | Source B (UK) | Source C (Japan) | Source D (Japan) | Source E (UK) | Source F (USA) | Source G (France) |
|---|---|---|---|---|---|---|---|
| Aluminium | 790 | 970 | 915 | 420 | 350 | 3190 | 155 |
| Copper | 2020 | 4510 | 23840 | 580 | 4830 | 1180 | 7910 |
| Iron | 41220 | 15200 | 23550 | 15240 | 7910 | 25920 | 1850 |
| Magnesium | 4500 | 500 | 15000 | 54000 | 1500 | 500 | 500 |
| Zinc | 7230 | 1650 | 930 | 4580 | 1520 | 3940 | 2130 |
| Manganese | 940 | 190 | 135 | 240 | 160 | 65 | 80 |

It can be seen that the average level of aluminium in the product of the invention was about 60 ng/g whereas the commercial sources had 155–3190 ng/g. Likewise, the product of the invention had an average of about 948 ng/g iron (compare 1850–41,200 ng/g in prior art material), an average of 2,990 ng/g of copper (compare 580–23,840 ng/g in prior art material), an average of 1,120 ng/g of magnesium (compare 500–54,000 ng/g in prior art material), an average of 2,390 ng/g of zinc (compare 930–7,230 ng/g in prior art material, and an average of 48 ng/g manganese (compare 65 to 940 ng/g in prior art material).

Analysis of Medium and Long Chain Fatty Acids

The fatty acids profiles of albumin according to the invention and commercially available HSA were analysed by acidic solvent extraction and gas chromatography of the free fatty acids using a C17:0 internal standard.

Equipment: Gas chromatograph (eg Shimadzu GC 9A) with flame ionisation detector; Autoinjector (eg Shimadzu AOC 14); Integrator/Printer (eg Shimadzu CR4A); HP-FFA 30×0.53 mm, 1.0 μm phase column (Hewlett Packard Ltd); Megabore Installation kit (J & W Scientific 220–1150 for GC 9A) with direct injection liner.

Reagents: Water (Milli-Q); Dichloromethane Super Purity Solvent (Romil Chemicals, Loughborough, Leics.); Sodium Acetate Trihydrate Analar (BDH Ltd. Poole); Acetic Acid Glacial Analar (BDH Ltd, Poole); Human Serum Albumin Solution (Zenalb™20, Bio Products Laboratory, Elstree, Herts.); Sodium Sulphate Anhydrous (Analytical Reagent); standard fatty acids from Sigma.

Solutions:

0.5M Sodium Acetate Buffer pH 4.5: Sodium Acetate 6.1³g and Acetic Acid 3.30g per 100 mi.

Free Fatty Acid standard mixtures. Weigh 5 mg of each fatty acid into separate glass vials. Dissolve each fatty acid in I ml Dichloromethane and transfer to three 12 ml Pyrex culture tubes respectively for short chain (C6–C14), medium chain (C16–C18) and long chain (C20–C22:1) fatty acids. Dry down mixture under a stream of nitrogen and dissolve in I ml Dichloromethane. Transfer 50 μl aliquots of mixture into labelled glass vials, dry under nitrogen, cap and store at −20° C. Internal Standard Solution 1 mg/ml Heptadecanoic Acid (25.0 mg Heptadecanoic Acid/25 ml Dichloromethane).

Procedure

1. Add 50 μl Internal Standard Solution to 6 labelled 40 ml Pyrex tubes.
2. For 5% rHA add 5 ml sample. For 25% rHA use 1 ml sample and 4 ml water. Include a blank (5 ml water) and serum albumin sample (1.25 ml Zenalb™20 and 3.75 ml water). Prepare all samples in duplicate.
3. Add 2.5 ml Sodium Acetate Buffer, then 10 ml Dichloromethane to all tubes.
4. Place the capped tubes on a mechanical roller for 2 hours at room temperature.
5. Centrifuge all tubes for 5 min at 3.000 rpm in a Sorvall RT6000B centrifuge at 20° C.
6. Remove the upper aqueous phase, then working from the bottom of the tube carefully transfer the lower Dichloromethane phase into a labelled 12 ml Pyrex tube. Protein globules may hinder the removal of all the Dichloromethane phase. If this occurs add a spatula full of Anhydrous Sodium Sulphate, cap and shake.
7. Dry Dichloromethane phase under a stream of nitrogen and store under nitrogen at −20° C. until analysis.
8. Install the capillary column and set the gas chromatograph to the following conditions according to the manufacturer's instructions:—Detector: Flame ionisation; Carrier Gas: Nitrogen at 30 ml min$^{-1}$; Injection Volume: 0.5 μl; Column initial temperature: 70° C.; Hold: 1.5 min; Gradient 1: 20° C. min$^{-1}$ to 150° C.; Gradient 2: 4° C. min-1 to 240° C.; Hold: 7 min; Detector Temperature: 280° C.; Setting Specific to Shimadzu GC9A are: Detector Range: $_{10}$°; Hydrogen Pressure: 0.5 kg/cm$^2$; Air Pressure: 0.5 kg/cm$^2$; Stop Time: 50 min.

9. Set up the integrator to collect data from the gas chromatograph according to the manufacturer's instructions.
10. Raise oven temperature to 245° C. and leave until a steady baseline is achieved.
11. Lower oven temperature to 70° C. and allow to equilibrate.
12. Thaw an aliquot of the Long, Medium and Short Chain Fatty Acid standards. Dissolve the Long Chain Fatty Acids in 1 ml Dichloromethane. Transfer the solution to the Medium Chain Fatty Acids and dissolve. Repeat for the Short Fatty Acids.
13. Inject the standard mixture to determine fatty acid retention times. The chromatogram produced should have very little peak tailing and have a smooth slowly rising baseline with the correct number of well resolved peaks. Caproic Acid (C6:0) should elute with a retention time of approx. 6 min and Erucic Acid (C22:1) with a retention time of approx. 33 min. Identify all peaks by comparison with example standard chromatogram.
14. Inject samples and collect data.

Calculations

1. Identify the internal standard peak from the blank samples. This will be the major peak with a retention time of approximately 23.5 min.
2. Calculate the Peak Area Ratios for all integrated peaks in all samples using the following formula.

Peak Area Ratio=Peak Area/Internal Standard Peak Area

Figure 4:
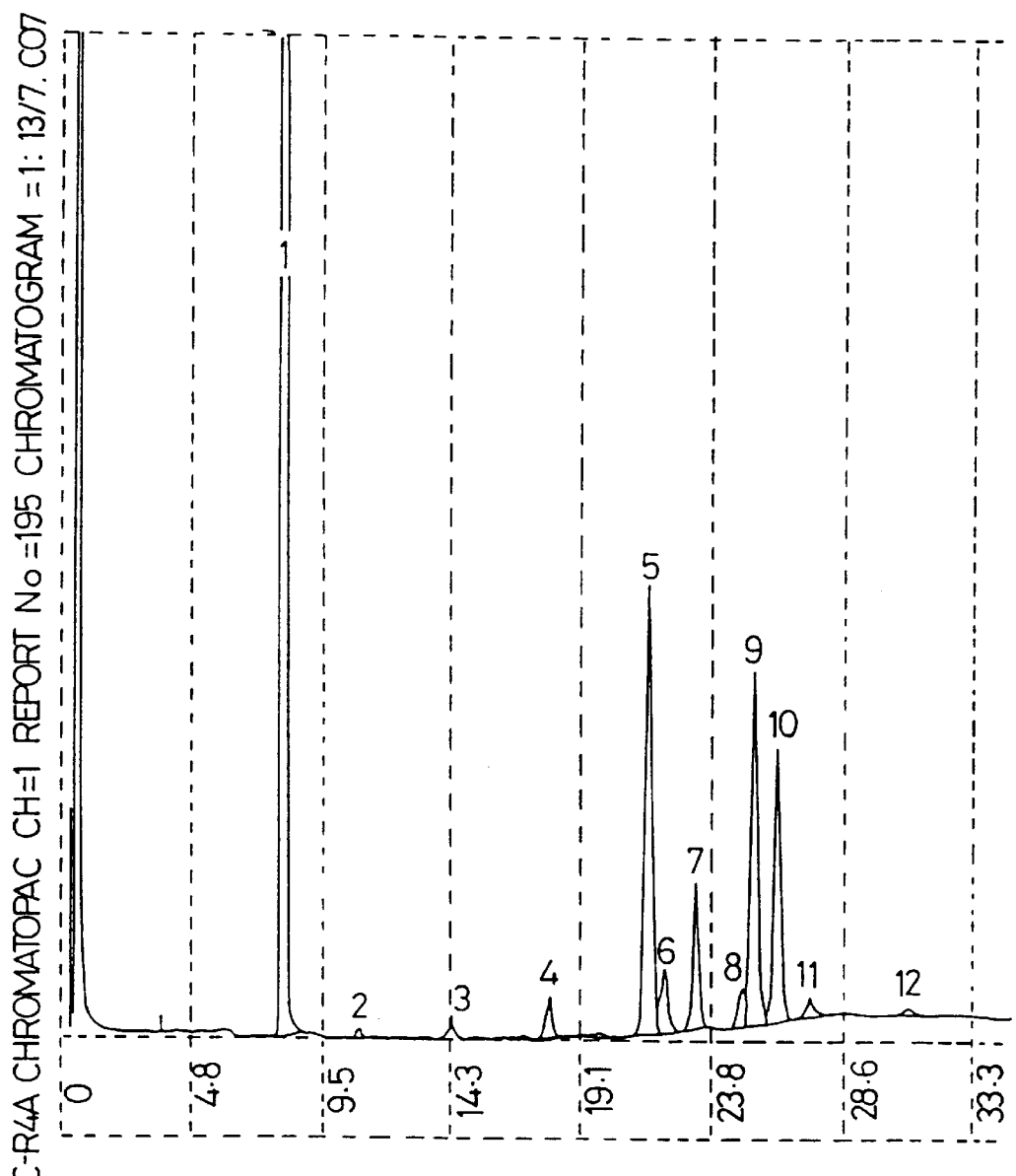
FIG. 4 is a gas chromatogram showing the fatty acid content of commercially available albumin.
Figure 5:
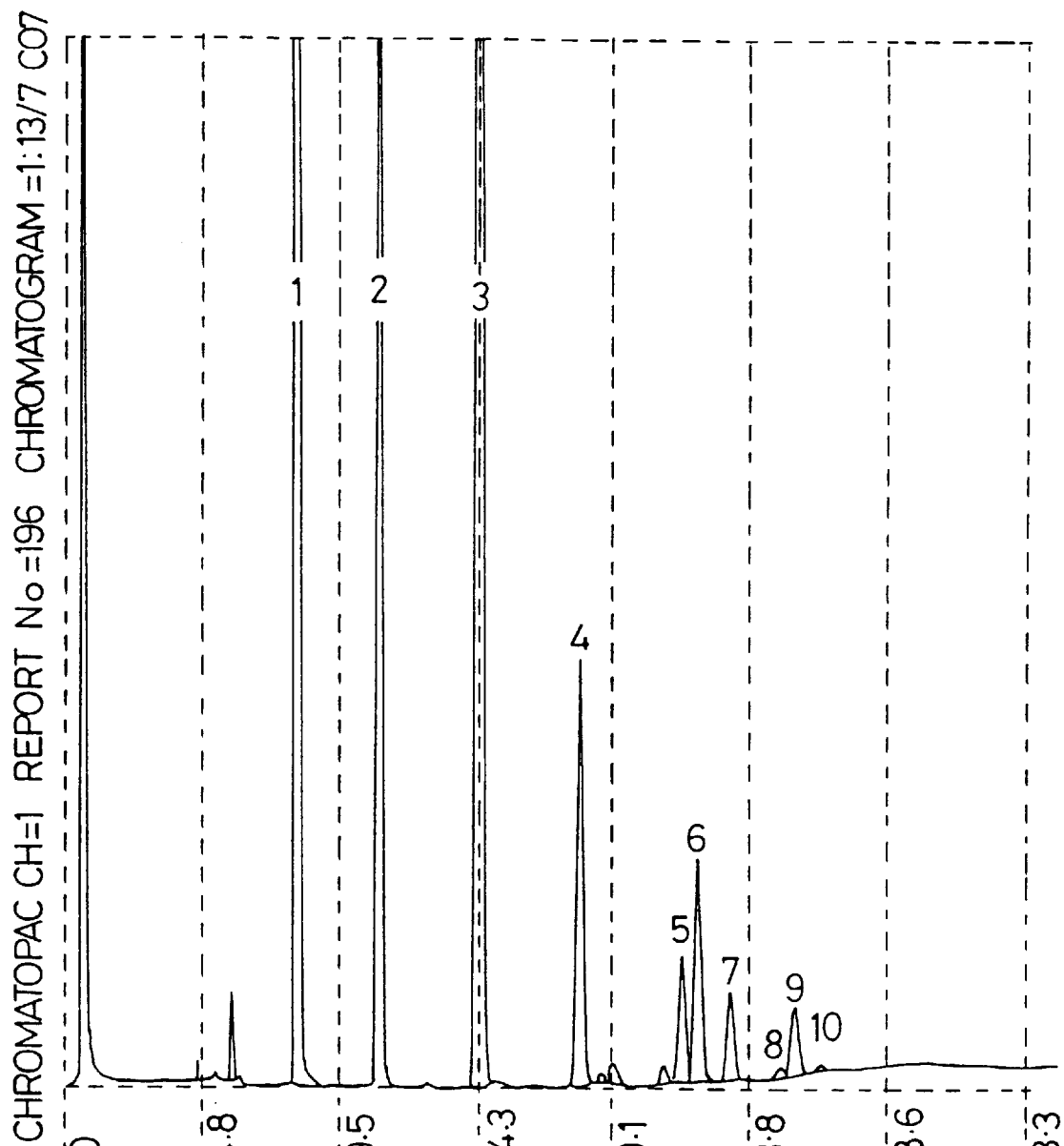
FIG. 5 corresponds to FIG. 4 but shows albumin of the invention.

3. Identify fatty acid peaks in rHA and HSA samples based on retention time by comparison with standards.
4. Convert all Peak Area Ratios to approximate concentrations ($\mu$g/g albumin) for both rHA and HSA samples using the following factor:—Concentration ($\mu$g/g)= Peak Area Ratio×200
5. For peaks identified as fatty acids convert Concentration from $\mu$g/g albumin to mole/mole albumin using the fatty acid's molecular weight and the following formula:

Concentration(mole/mole)=Concentration ($\mu$g/g)×0.0665/Fatty Acid Molecular Weight Example results are presented for a batch of albumin prepared according to Example 2 (FIG. 4) and commercial HSA (FIG. 5). No abnormal fatty acids have been detected in the former by this method although the profiles for the two proteins showed significant differences. As expected, both showed large amounts of the added stabiliser, octanoate (C8:0). Apart from this, commercial HSA was characterised by predominantly C16:0, C16:1. C18:0, C18:1 and C18:2 whilst the albumin of the invention contained mainly C10:0, C12:0, C16:1 and occasionally C14:0. Further experiments showed that the levels of CIO:0 and C12:0 in rHA final product correlated with the levels of these contaminants in the octanoate used for the latter stages of the purification process.

Data for the rHA produced according to Example 7 are as follows:

TABLE 11

Comparison of the fatty acid composition of rHA purified according to the process of the invention and commercial HSA.
Fatty acid content (mol/mol protein)

| Fatty acid | rHA | HSA |
| --- | --- | --- |
| C10:0 | 0.100 | 0.005 |
| C12:0 | 0.020 | 0.011 |
| C14:0 | 0.005 | 0.017 |
| C16:0 | 0.013 | 0.152 |
| C16:1 | 0.064 | 0.023 |
| C18:0 | 0.002 | 0.024 |
| C18:1 | 0.012 | 0.145 |
| C18:2 | ND | 0.089 |
| C18:3 | ND | 0.006 |
| C20:0 | ND | 0.001 |
| C20:1 | ND | 0.001 |
| C20:2 | ND | ND |
| C20:4 | ND | 0.006 |
| TOTAL | 0.216 | 0.480 |

ND = Not detected.

Preferably, the total level of C18 fatty acids does not exceed 1.0% (mole/mole) of the level of octanoate, and preferably does not exceed 0.5% of that level. Moreover. in the albumin of the invention, the level of C18:2. C18:3 and C20 fatty acids is generally undetectable. In commercial HSA, there may typically be about 0.4 moles C10 to C20 fatty acids per mole of albumin. In the product of the invention, there is typically no detectable C20 fatty acids and only about 0.01 to 0.02 moles C18 fatty acids per mole of albumin.

Analysis of Colour—The absorbance of a 5% (w/v) solution of the final product in a 1 cm cuvette was measured at 350 nm, 403 nm and 500 nm and calculated in terms of absorbances per gram of albumin/litre per cm pathlength (ie A L.g$^{-1}$.cm$^{-1}$). The albumin of the invention has the following values:

| Wavelength (nm) | Mean absorbance (n = 10 batches) (L.g$^{-1}$.cm$^{-1}$) |
| --- | --- |
| 350 | 4.74 × 10$^{-3}$ |
| 403 | 2.12 × 10$^{-3}$ |
| 500 | 0.58 × 10$^{-3}$ |

Generally, the albumin of the invention does not exceed respective absorbances of 6.0×10$^{-3}$, 2.5×10$^{-3}$ and 0.75×10$^{-3}$ at the said three wavelengths.

Assays of a number of commercially available HSA preparations revealed higher absorbances at these wavelengths (see Table 12).

TABLE 12

Absorbance (L.g$^{-1}$.cm$^{-1}$) of prior art HSA preparations

| SAMPLE | A$_{350}$ | A$_{403}$ | A$_{500}$ |
| --- | --- | --- | --- |
| 1 | 9.95 | 4.10 | 0.8 |
| 2 | 9.25 | 5.36 | 1.1 |
| 3 | 7.40 | 3.26 | 0.6 |
| 4 | 7.20 | 3.60 | 0.6 |
| 5 | 8.68 | 4.08 | 0.8 |
| 6 | 11.45 | 6.26 | 1.2 |
| 7 | 7.20 | 3.70 | 0.8 |
| 8 | 6.82 | 4.78 | 1.8 |

SDS reducing polyacrylamide gel electrophoresis—This assay is performed to show that rHA consists of a single polypeptide chain which when treated with a reducing agent (β-mercaptoethanol) migrates as a single band (monomer) on SDS reducing polyacrylamide electrophoresis (PAGE).

Samples of albumin were boiled in SDS reducing buffer (20 mM Tris-HCI pH 8.0 containing 2 mM EDTA, 5% (w/v) SDS and 10% (v/v) β-mercaptoethanol with the albumin at 1 mg/ml, and then separated on SDS homogeneous (12.5%) Phastgels (Pharmacia), using a loading of 1 µl of the solution. Protein bands were detected by Coomassie Blue R250 staining, scanned on a Shimadzu CS9000 densitometer. Separation of albumin showed a single band of Coomassie staining which is indicative that the proportion of albumin present as a monomer is at least 99.9%.

Gel permeation high pressure liquid chromatography

25 µl of a 10 mg/ml solution of the albumin in the eluate from the anion exchange matrix in the main embodiment of the process of the invention (ie where the anion exchange step is the final step before ultrafiltration and formulation) is injected onto a TSK3000SWXL column on a Shimadzu LC6A HPLC. The product was found to be at least 99.9% monomeric.

25 µl of a second 10 mg/ml solution of albumin purified in accordance with the invention which had been formulated to 25% w/v was assayed in the same manner and found to contain less than 0.1% polymeric albumin. This result indicates that the formulation as described herein has no effect on the polymer/aggregate content of the purified albumin.

Two Dimensional Gel Electrophoresis

2 µg rHA of albumin prepared by the process of the invention was subject to two-dimensional electrophoresis using a Millipore Investigator system. The separation in the first dimension was a pH 3–10 isoelectric focusing gel and was followed by a 10% polyacrylamide/SDS gel in the second dimension. On staining of the gel with Coomassie Blue, only one spot was visible, indicating the presence of only one protein species.

Electrospray ass Spectrometry

Electrospray mass spectrometry (ESMS) was performed using a VG Quattro electrospray mass spectrometer, calibrated with horse heart myoglobin (16951 Da, obtained from Sigma) over m/z range 950–1750 Da/e. Samples of commercially available HSA and samples of rHA purified according to the invention were desalted prior to analysis by reverse phase HPLC using an acetonitrile gradient containing trifluoroacetic acid. FIGS. 6a and b show the spectra for albumin of the invention and prior art HSA, respectively. The latter shows peaks representing blocked free thiol and N-terminal degradation.

The albumin of the invention can be seen to be substantially homogeneous in this assay, in other words it shows a single defined peak, occurring at a mass of about 66441 Da.

Long term stability

Over two years, no degradation of the albumin is detectable by electrophoretic methods, which shows that no protease activity is present.

What is claimed is:

1. A process for purifying albumin, the process comprising the steps of:
   (a) passing an impure albumin solution through a chromatographic material for which the albumin has no specific affinity under conditions such that the albumin will bind to the chromatographic material and low molecular weight species will pass directly through the material; and
   (b) eluting the bound albumin from the chromatographic material by passing through the chromatographic material a solution of a compound having a specific affinity for albumin, to yield a purified albumin solution.

2. A process according to claim 1 wherein the albumin-containing solution obtained thereby is, with or without intervening process steps, ultrafiltered through an ultrafiltration membrane to obtain an ultrafiltration retentate having an albumin concentration of at least 80 g albumin per litre and the ultrafiltration retentate is diafiltered against at least 5 retentate equivalents of water.

3. A process according to claim 1 wherein the albumin obtained thereby is formulated for intravenous administration to a human.

4. A process according to claim 1 wherein albumin obtained thereby is then, with or without intervening process steps, subjected to chromatography on a resin containing an immobilized compound which will selectively bind glycoconjugates and saccharides.

5. A process according to claim 4 wherein the immobilized compound is aminophenylboronic acid (PBA).

6. A process according to claim 1 wherein the albumin obtained thereby is further purified.

7. A process according to claim 6 wherein the albumin obtained thereby is formulated for intravenous administration to a human.

8. A process according to claim 1 wherein the relatively impure albumin solution is obtained from a yeast culture medium obtained by culturing yeast transformed with an albumin-encoding nucleotide sequence in a fermentation medium, whereby said yeast expresses and secretes albumin.

9. A process according to claim 8 wherein the yeast is separated from the fermentation medium before the medium is applied to the cation exchange matrix.

10. A process according to claim 8, wherein said fermentation medium is free of a metal-chelating agent.

11. A process according to claim 10 wherein the yeast is separated from the fermentation medium before the medium is applied to the cation exchange matrix.

12. A process according to claim 1 in which the chromatographic material is a cation exchanger resin.

13. A process according to claim 12, wherein, prior to applying the relatively impure albumin solution to said cation exchanger resin, the albumin solution is conditioned by adding octanoate thereto to a final concentration of from about 1–10 mM and adjusting the pH to between about 4.0 to 5.0.

14. A process according to claim 12 wherein albumin obtained thereby is then, with or without intervening process steps, subjected to chromatography on a resin containing an immobilized compound which will selectively bind glycoconjugates and saccharides.

15. A process according to claim 12 wherein the compound is a fatty acid salt.

16. A process according to claim 15 wherein the fatty acid salt is octanoate.

17. A process for purifying albumin, comprising the steps of:
   (a) passing an albumin solution through a cation exchange matrix under conditions such that the albumin will bind to the matrix;
   (b) eluting from said matrix an albumin-containing cation exchange eluate;
   (c) passing said eluate through an affinity matrix comprising an albumin-binding compound;
   (d) eluting from the affinity matrix an albumin-containing affinity matrix eluate;
   (e) passing said eluate through a gel permeation matrix to obtain a fraction enriched in albumin;
   (f) passing said albumin-enriched fraction through an anion exchange matrix under conditions such that albumin will bind to the anion exchange matrix; and
   (g) eluting from said anion exchange matrix a purified albumin-containing product.

18. The process of claim 17 wherein an ultrafiltration step is performed between said eluting step (d) and said gel permeation matrix step (e).

19. A process according to claim 17 wherein, prior to passing an albumin solution through said cation exchanger matrix, the albumin solution is conditioned by adding octanoate thereto to a final concentration of from about 1–10 mM and adjusting the pH so that it is between about 4.0 and about 5.0.

20. A process according to claim 17, wherein the albumin-containing solution obtained thereby is, with or without intervening process steps, ultrafiltered through an ultrafiltration membrane to obtain an ultrafiltration retentate having an albumin concentration of at least 80 g albumin per litre and the ultrafiltration retentate is diafiltered against at least 5 retentate equivalents of water.

21. A process according to claim 17 wherein the albumin obtained thereby is formulated for intravenous administration to a human.

22. A process according to claim 17 wherein the albumin obtained thereby is further purified.

23. A process according to claim 22 wherein the albumin obtained thereby is formulated for intravenous administration to a human.

24. A process for purifying albumin, comprising the steps of:
   (a) passing an albumin solution through a cation exchange matrix under conditions such that the albumin will bind to the matrix;

(b) eluting from the matrix an albumin-containing cation exchange eluate;

(c) passing the cation exchange eluate through an anion exchange matrix under conditions such that the albumin will bind to the matrix;

(d) eluting from the anion exchange matrix an albumin-containing anion exchange eluate;

(e) passing the anion exchange eluate through an affinity matrix comprising an albumin-binding compound;

(f) eluting from the affinity matrix an albumin-containing affinity matrix eluate; and (g) passing the affinity matrix eluate through a gel permeation matrix to obtain a fraction enriched in albumin.

25. A process according to claim 24 wherein, prior to passing an albumin solution through said cation exchanger matrix, the albumin solution is conditioned by adding octanoate thereto to a final concentration of from about 1–10 mM and adjusting the pH to between about 4.0 to 5.0.

26. A process according to claim 24, wherein the albumin-containing solution obtained thereby is, with or without intervening process steps, ultrafiltered through an ultrafiltration membrane to obtain an ultrafiltration retentate having an albumin concentration of at least 80 g albumin per litre and the ultrafiltration retentate is diafiltered against at least 5 retentate equivalents of water.

27. A process according to claim 24 wherein the albumin obtained thereby is formulated for intravenous administration to a human.

28. A process according to claim 24 wherein the albumin obtained thereby is further purified.

29. A process according to claim 28 wherein the albumin obtained thereby is formulated for intravenous administration to a human.

30. A process according to claim 24 wherein the albumin is eluted in the cation exchange step using a buffer containing a compound having a specific affinity for albumin.

31. A process according to claim 30 wherein the compound is an octanoate salt.

32. A process according to claim 30 wherein the albumin in the cation exchange step is washed with a high salt solution before being eluted.

33. A method of removing ammonium ions bound to albumin in an albumin solution, the method comprising (a) exposing the albumin solution to a solution of a counter-ion such that ammonium ions are displaced from the albumin and (b) removing the ammonium ions from the albumin solution.

34. A method according to claim 33 which the counter-ion solution is added to the albumin solution and the ammonium ions are removed by dialysis.

35. A method according to claim 33 in which the counter-ion solution is separated from the albumin solution by a semi-permeable membrane and the ammonium ions are removed by diafiltration.

36. A method according to claim 33 in which the ammonium ions are removed from the solution by gel permeation chromatography.

37. A method according to claim 33 in which the counter-ion solution is a solution comprising sodium ions.

38. A method of purifying an albumin solution, the method comprising exposing the solution to a chromatographic material in a buffer containing ammonium ions, and subsequently removing the ammonium ions by a method according to claim 33.

39. A method according to claim 38 in which the chromatographic material comprises immobilised borate ions.

40. A method of purifying intact albumin from a solution which contains the intact albumin and an approximately 45 kD albumin fragment, the method comprising (a) passing the solution through a chromatographic material comprising an immobilized dye having specific affinity for albumin such that the albumin in the solution binds to the dye; and (b) selectively eluting the bound intact albumin from the bound 45 kD albumin fragment, to yield purified intact albumin.

41. A method according to claim 40 wherein the dye is a polysulfonated anthraquinone triazine dye.

42. A process according to claim 41 wherein said dye is immobilized on a resin via a spacer.

43. A process according to claim 42 wherein the spacer is an $\alpha,\omega$-diamino-($C_{1-6}$ straight chain alkyl) group.

44. A process for purifying albumin, the process comprising the steps of:

(a) subjecting an albumin solution to cation exchange chromatography in which the albumin is bound to a cation exchange material and then eluted therefrom;

(b) treating the albumin eluted in step (a) by one or more processes selected from the group consisting of affinity chromatography, ultrafiltration, and gel filtration; and (c) treating the albumin obtained from step (b) to anion exchange chromatography in which the albumin is bound to an anion exchange material.

45. A process according to claim 44 wherein albumin obtained thereby is then, with or without intervening process steps, subjected to chromatography on a resin containing an immobilized compound which will selectively bind glycoconjugates and saccharides.

46. A process according to claim 44 wherein the affinity chromatography uses a resin comprising an immobilized albumin-specific dye.

47. A process according to claim 46 wherein the dye is a polysulfonated anthraquinone triazine dye.

48. A process according to claim 47 wherein the dye is immobilized on the resin via a spacer.

49. A process according to claim 48 wherein the spacer is an $\alpha,\omega$-diamino-($C_{1-6}$ straight chain alkyl) group.

50. A process for purifying albumin, the process comprising the steps of:

(a) subjecting an albumin solution to cation exchange chromatography in which the albumin is bound to a cation exchange material and then eluted therefrom; and (b) subjecting the albumin eluted from the cation exchange material in step (a) to anion exchange chromatography in which the albumin is bound to an anion exchange material without any intervening treatment between steps (a) and (b) or without any intervening treatment other than dilution of the albumin.

51. A process according to claim 50 wherein the albumin is eluted from the anion exchanger with a buffer containing 50–200 mM boric acid salt.

52. A process according to claim 50 wherein albumin obtained thereby is then, with or without intervening process steps, subjected to chromatography on a resin containing an immobilized compound which will selectively bind glycoconjugates and saccharides.

53. A process according to claim 50 wherein the albumin is eluted in the cation exchange step using a buffer containing a compound having a specific affinity for albumin.

54. A process according to claim 53 wherein the albumin in the cation exchange step is washed with a high salt solution before being eluted.

55. A process according to claim 53 wherein the compound is an octanoate salt.

56. A process according to claim 55 wherein the albumin in the cation exchange step is washed with a high salt solution before being eluted.

57. A process for purifying albumin in an impure albumin solution from a macromolecule with a carbohydrate moiety, the process comprising the steps of: (a) passing the impure albumin solution through a chromatographic material comprising a boronic acid or salt thereof such that the macromolecule with the carbohydrate moiety binds to the chromatographic material; and (b) eluting the albumin from the chromatographic material, to yield a purified albumin solution.

58. A process according to claim 57 wherein the purified albumin is further purified and formulated for intravenous administration to a human.

59. A process according to claim 57 wherein the albumin obtained thereby is formulated for intravenous administration to a human.

60. A process according to claim 57 wherein the albumin solution contains a compound selected from the group consisting of glycoconjugates and saccharides.

61. A process according to claim 60 wherein the albumin solution contains a glycoconjugate, said glycoconjugate comprising a yeast glycoprotein.

62. A process according to claim 57 wherein the boronic acid is aminophenylboronic acid or a salt thereof.

63. A process according to claim 62 wherein the aminophenylboronic acid is immobilized on an agarose gel.

64. A process according to claim 57 wherein the albumin solution is buffered with one or more ions selected from the group consisting of acetate ions, chloride ions, octanoate ions and ammonium ions.

65. A process according to claim 64 wherein the solution contains 10–100 mM acetate ions. 10–100 mM ammonium ions, 20–2000 mM chloride ions and 1–20 mM octanoate ions and has a pH of 9.0–9.5.

66. A process according to claim 57 wherein the albumin obtained thereby is further purified.

67. A process according to claim 66 wherein the albumin obtained thereby is formulated for intravenous administration to a human.

* * * * *